(12) United States Patent
Caldwell

(10) Patent No.: US 9,895,308 B2
(45) Date of Patent: Feb. 20, 2018

(54) HETEROCYCLIC COMPOUNDS AND THEIR USES

(71) Applicant: AMGEN INC., Thousand Oaks, CA (US)

(72) Inventor: William Brett Caldwell, Bend, OR (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/773,444

(22) PCT Filed: Mar. 14, 2014

(86) PCT No.: PCT/US2014/027061
§ 371 (c)(1),
(2) Date: Sep. 8, 2015

(87) PCT Pub. No.: WO2014/152198
PCT Pub. Date: Sep. 25, 2014

(65) Prior Publication Data
US 2016/0015628 A1  Jan. 21, 2016

Related U.S. Application Data

(60) Provisional application No. 61/785,492, filed on Mar. 14, 2013.

(51) Int. Cl.
*A61K 9/00* (2006.01)
*A61K 9/28* (2006.01)
*A61K 31/496* (2006.01)
*A61K 9/20* (2006.01)

(52) U.S. Cl.
CPC .......... *A61K 9/0004* (2013.01); *A61K 9/2866* (2013.01); *A61K 31/496* (2013.01); *A61K 9/2054* (2013.01)

(58) Field of Classification Search
CPC .... A61K 31/496; A61K 9/2054; A61K 47/38; A61K 9/0004; A61K 9/2013; A61K 9/2018; A61K 9/2866; C07D 213/75
See application file for complete search history.

(56) References Cited

U.S. PATENT DOCUMENTS

| 5,612,059 A | 3/1997 | Cardinal et al. |
| 5,698,220 A | 12/1997 | Cardinal et al. |
| 7,507,735 B2 | 3/2009 | Morgan et al. |
| 8,197,846 B2 | 6/2012 | Sako et al. |
| 2007/0161617 A1* | 7/2007 | Morgan ............... A61K 31/496 514/210.2 |
| 2011/0182947 A1* | 7/2011 | Appel .................. A61K 9/0004 424/400 |

FOREIGN PATENT DOCUMENTS

| WO | WO-2001/047500 A1 | 7/2001 |
| WO | WO-2007/070683 A2 | 6/2007 |

OTHER PUBLICATIONS

International Search Report and Written Opinion of the International Searching Authority in connection with International Application PCT/US2014/027061, United States Patent Office, dated Mar. 14, 2014.

* cited by examiner

*Primary Examiner* — Mark V Stevens
(74) *Attorney, Agent, or Firm* — Marshall, Gerstein & Borun LLP

(57) ABSTRACT

Provided are certain pharmaceutical formulations of omecamtiv mecarbil and methods for their preparation and use.

15 Claims, 8 Drawing Sheets

|  | IR (N = 20) | SCT-F1 (N = 21) | SCT-F2 (N = 21) |
|---|---|---|---|
| Potency | 0.979 | 0.914 | 0.910 |
| $T_{max}$ (h)[#] | 0.5 (0.5 - 1) | 10 (4 – 24) | 6 (2 – 10) |
| $C_{max}$ (ng/mL) | 269 (30.7) (138 – 449) | 37.3 (28.6) (21.0 – 57.5) | 72.2 (26.3) (36.0 – 95.9) |
| $AUC_{last}$ (ng.h/mL) | 2451 (20.0) (1787 – 3565) | 1455 (40.0) (805 – 2812) | 2074 (20.0) (1269 – 3104) |
| $AUC_{inf}$ (ng.h/mL) | 2509 (17.1) (1819 – 3782) | 1523 (37.1) (853 – 3212) | 2144 (23.5) (1304 – 3411) |
| $t_{1/2}$ (h) | 19 (20.6) (12.2 – 25.3) | 19.5 (23.5) (11.7 – 30.3) | 19.7 (18.2) (12.9 – 31.5) |
| RBA (rel to IR)* | -- | 0.61 [0.57 – 0.65] | 0.88 [0.82 – 0.94] | data presented as median (%CV) (range)
: median(range)
RBA: relative bioavailability; * Geo mean (90% CI)

FIGURE 4

HETEROCYCLIC COMPOUNDS AND THEIR USES

CROSS REFERENCE TO RELATED APPLICATIONS

The benefit of U.S. Provisional Application No. 61/785,492, filed Mar. 14, 2013, is claimed, the disclosure of which is incorporated by reference in its entirety.

FIELD

Provided is a pharmaceutical formulation comprising omecamtiv mecarbil, or a pharmaceutically acceptable salt, a pharmaceutically acceptable hydrate, or a pharmaceutically acceptable hydrate of a pharmaceutically acceptable salt thereof, such as omecamtiv mecarbil dihydrochloride hydrate.

BACKGROUND

The cardiac sarcomere is the basic unit of muscle contraction in the heart. The cardiac sarcomere is a highly ordered cytoskeletal structure composed of cardiac muscle myosin, actin and a set of regulatory proteins. The discovery and development of small molecule cardiac muscle myosin activators would lead to promising treatments for acute and chronic heart failure. Cardiac muscle myosin is the cytoskeletal motor protein in the cardiac muscle cell. It is directly responsible for converting chemical energy into the mechanical force, resulting in cardiac muscle contraction.

Current positive inotropic agents, such as beta-adrenergic receptor agonists or inhibitors of phosphodiesterase activity, increase the concentration of intracellular calcium, thereby increasing cardiac sarcomere contractility. However, the increase in calcium levels increase the velocity of cardiac muscle contraction and shortens systolic ejection time, which has been linked to potentially life-threatening side effects. In contrast, cardiac muscle myosin activators work by a mechanism that directly stimulates the activity of the cardiac muscle myosin motor protein, without increasing the intracellular calcium concentration. They accelerate the rate-limiting step of the myosin enzymatic cycle and shift it in favor of the force-producing state. Rather than increasing the velocity of cardiac contraction, this mechanism instead lengthens the systolic ejection time, which results in increased cardiac muscle contractility and cardiac output in a potentially more oxygen-efficient manner.

U.S. Pat. No. 7,507,735, herein incorporated by reference, discloses a genus of compounds, including omecamtiv mecarbil (AMG 423, CK-1827452), having the structure:

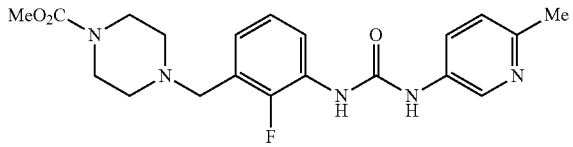 [SMILES: COC(=O)N1CCN(Cc2cccc(NC(=O)Nc3ccc(C)nc3)c2F)CC1]

Omecamtiv mecarbil is a first in class direct activator of cardiac myosin, the motor protein that causes cardiac contraction. It is being evaluated as a potential treatment of heart failure in both intravenous and oral formulations with the goal of establishing a new continuum of care for patients in both the in-hospital and outpatient settings.

Clinical trials providing an I.V. delivery of omecamtiv mecarbil have shown that plasma levels of the drug can be delivered safely and effectively. However, standard release formulations and some extended release formulations gave peak to trough ratios that may be too great to provide a safe and effective amount of omecamtiv mecarbil to patients who need the drug in a chronic or preventative setting (See, FIG. 3). Accordingly, an effective sustained release formulation would be desirable for increased patient safety and effectiveness.

SUMMARY

Provided is a pharmaceutical formulation comprising:
 a drug layer comprising omecamtiv mecarbil, or a pharmaceutically acceptable salt, a pharmaceutically acceptable hydrate, or a pharmaceutically acceptable hydrate of a pharmaceutically acceptable salt thereof;
 a sweller layer; and
 a semi-permeable membrane coating having at least one delivery port.

Also provided are methods for the preparation of such pharmaceutical formulations.

Also provided are methods for the use of such pharmaceutical formulations for the treatment of heart failure.

DESCRIPTION OF THE FIGURES

FIG. 4 is a table with pharmacokinetic data for an immediate release composition and two pharmaceutical formulations described herein.

DETAILED DESCRIPTION

Figure 1:
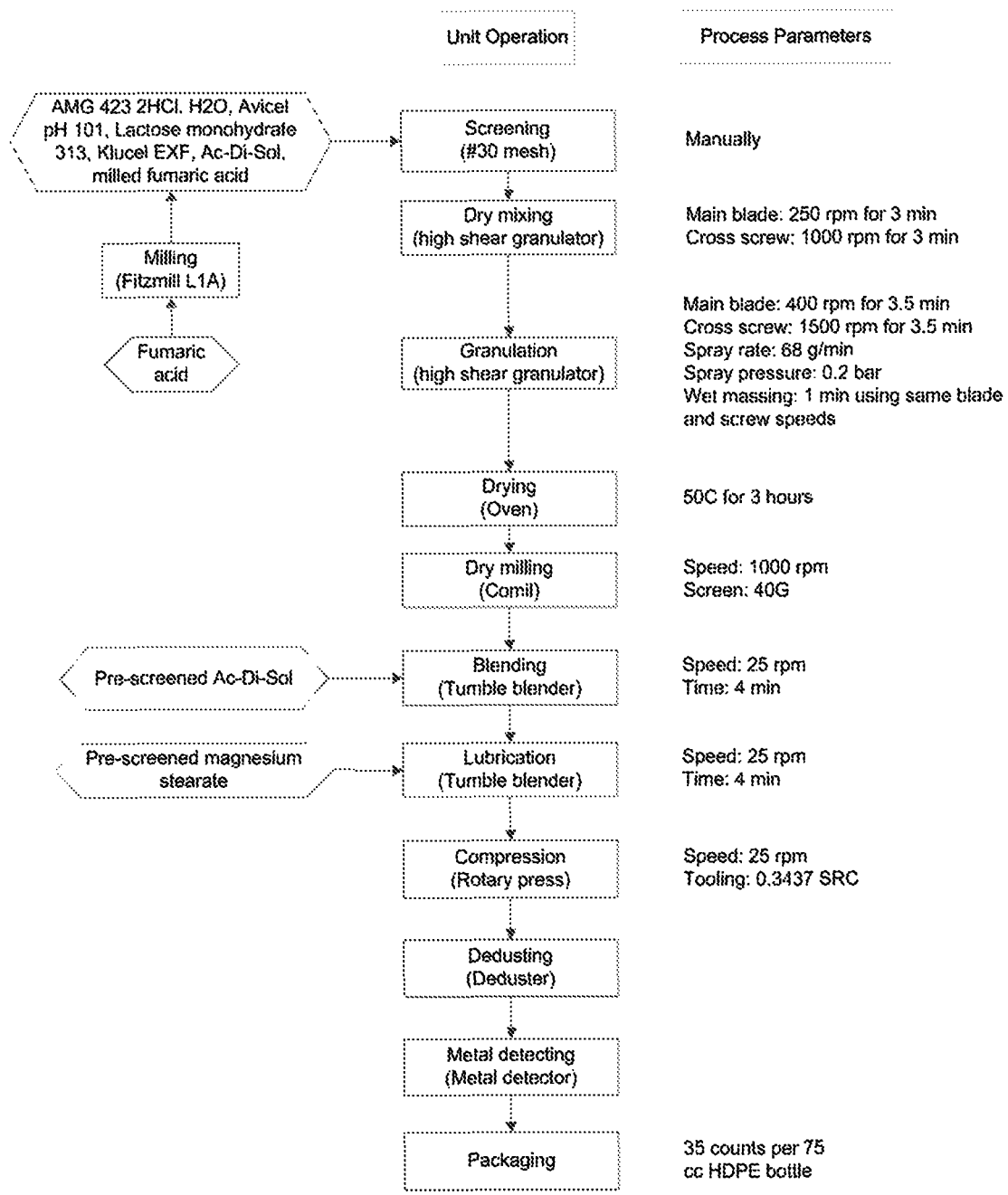
FIG. 1 is a flow diagram for the preparation of immediate release (IR) tablets of omecamtiv mecarbil (25 mg).
Figure 2:
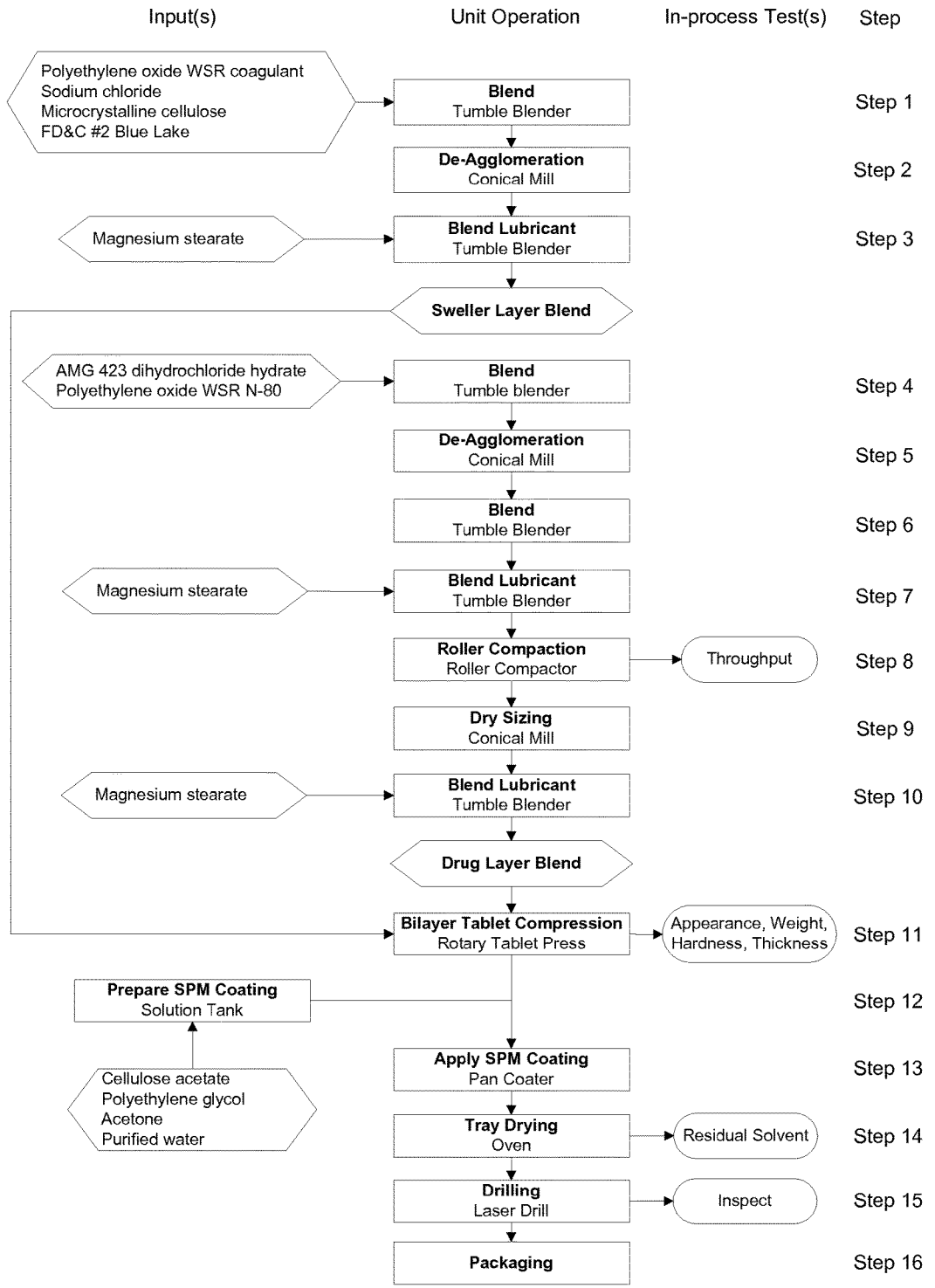
FIG. 2 is a flow diagram for the preparation of omecamtiv mecarbil dihydrochloride hydrate 25-mg MR Swellable Core (F1 and F2) Tablets.
Figure 3:
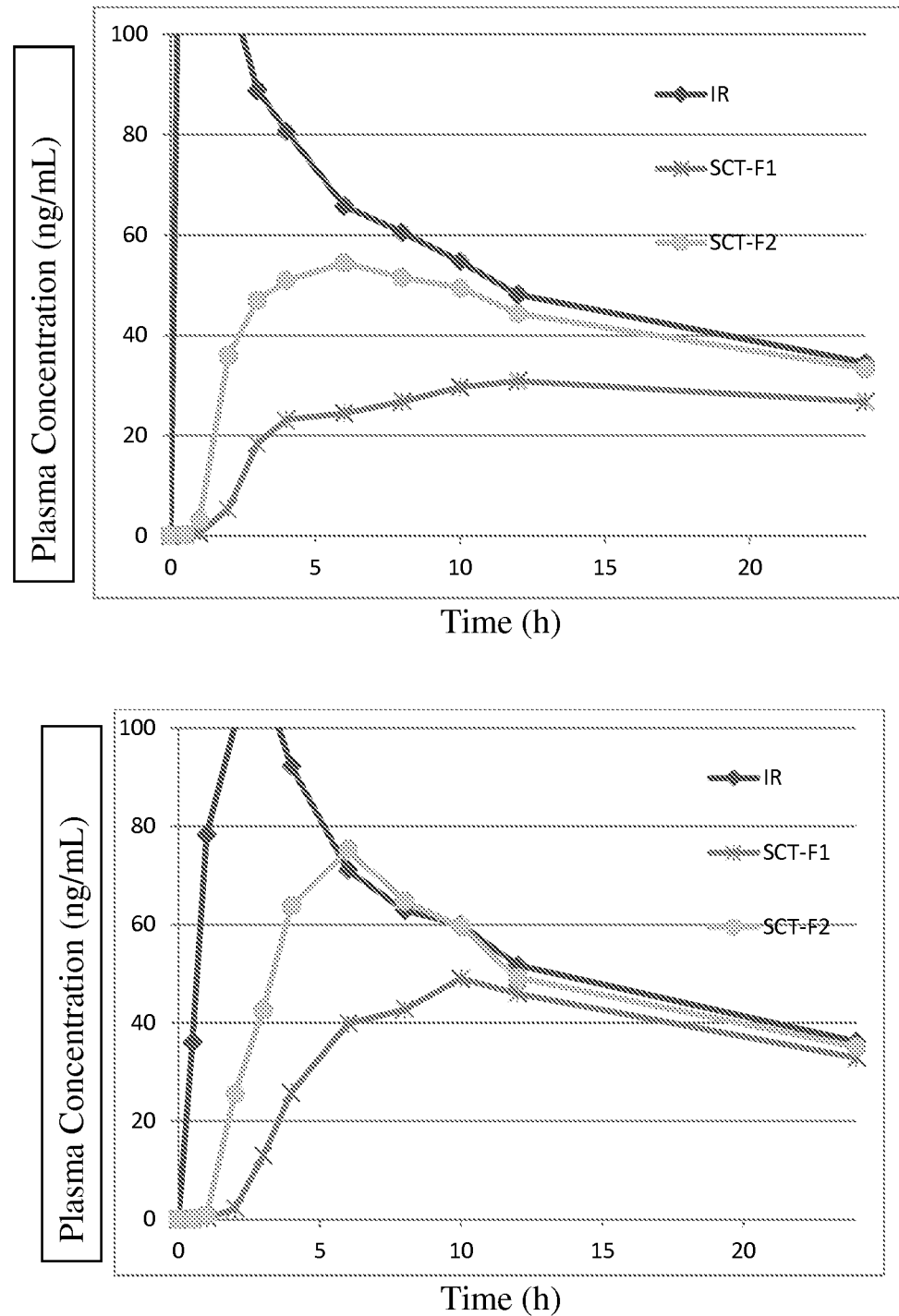
FIG. 3 shows the exposure of healthy volunteers (plasma concentration (ng/ml) v. time (h)), fasted (top) and fed (bottom) for an immediate release (IR) composition and two pharmaceutical formulations with different release profiles described herein (Swellable Core Tablet—release profile 1=SCT-F1, Swellable Core Tablet—release profile 2=SCT-F2). The study was a randomized, open-label, 4-way cross-over incomplete block design study in healthy adult subjects:
 60 subjects; 1 site in the US
 12 total treatments (each treatment taken 20 times)
 Various formulations; Each taken fasted or fed
 Each subject will be randomized to 1 sequence
 Each subject receives 4 out of 12 possible treatments
 Each period ~7 days; Study duration: 27 days (Period 4: 5 days)

Unless otherwise specified, the following definitions apply to terms found in the specification and claims:

"Treatment" or "treating" means any treatment of a disease in a patient, including: a) preventing the disease, that is, causing the clinical symptoms of the disease not to develop; b) inhibiting the disease; c) slowing or arresting the development of clinical symptoms; and/or d) relieving the disease, that is, causing the regression of clinical symptoms. Treatment of diseases and disorders herein is intended to also include the prophylactic administration of a pharmaceutical formulation described herein to a subject (i.e., an animal, preferably a mammal, most preferably a human) believed to be in need of preventative treatment, such as, for example, chronic heart failure.

The term "therapeutically effective amount" means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

"Pharmaceutically acceptable salts" include, but are not limited to salts with inorganic acids, such as hydrochlorate (i.e., hydrochloride), phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium. Those skilled in the art will recognize various synthetic methodologies that may be used to prepare non-toxic pharmaceutically acceptable addition salts.

The term "hydrate" refers to the chemical entity formed by the interaction of water and a compound, including, for example, hemi-hydrates, monohydrates, dihydrates, trihydrates, etc.

"Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Provided is a pharmaceutical formulation comprising omecamtiv mecarbil, or a pharmaceutically acceptable salt, a pharmaceutically acceptable hydrate, or a pharmaceutically acceptable hydrate of a pharmaceutically acceptable salt thereof, such as omecamtiv mecarbil dihydrochloride hydrate.

The pharmaceutical formulations described herein exhibit reduced plasma concentration fluctuation (as shown in FIG. 4), which is expected to lead to reduced side effects, and improved safety and efficacy. It is also expected that the pharmaceutical formulations described herein will improve patient compliance by reducing the dosing frequency. Additionally, the pharmaceutical formulations described herein are physicochemically stable.

In some embodiments, in conjunction with other above or below embodiments, the pharmaceutical formulations described herein start releasing drug soon after introduction to the use environment. In some embodiments, in conjunction with other above or below embodiments, the pharmaceutical formulations release at least 5 wt % of the drug, such as at least 10 wt % of the drug within 2 hours after introduction to the use environment, where these percentages correspond to the mass of drug released from the core relative to the total mass of drug originally present in the core. By quickly beginning the release of the drug, the dosage form shortens the time required to achieve a maximum drug concentration in a use environment and increases the total amount of time during which the drug is in a use environment, resulting in increased absorption and greater bioavailability.

In some embodiments, in conjunction with other above or below embodiments, the pharmaceutical formulations release the drug in a controlled manner, such as at a substantially constant rate. Thus, in some embodiments, in conjunction with other above or below embodiments, the pharmaceutical formulations release no more than about 60 wt % of the drug, for example, no more than about 50 wt % of the drug, into the use environment within 2 hours after introduction to the use environment.

In some embodiments, in conjunction with other above or below embodiments, the rate of release of drug from the pharmaceutical formulations is sufficiently high to allow release of the drug within a time frame that allows a substantial fraction of the drug delivered to be absorbed into the blood stream. In some embodiments, in conjunction with other above or below embodiments, the pharmaceutical formulations release at least 60 wt % of the drug, such as at least 70 wt % of the drug, to the use environment within 16 hours after introduction to the use environment.

In some embodiments, in conjunction with other above or below embodiments, the pharmaceutical formulations release a substantial amount of the drug contained within the pharmaceutical formulations, leaving a relatively small residual amount of drug after 24 hours.

In some embodiments, in conjunction with other above or below embodiments, the pharmaceutical formulation comprises a bilayer, wherein the omecamtiv mecarbil, or a pharmaceutically acceptable salt, a pharmaceutically acceptable hydrate, or a pharmaceutically acceptable hydrate of a pharmaceutically acceptable salt thereof, such as omecamtiv mecarbil dihydrochloride hydrate, is dispersed in a hydrophilic polymer matrix in one layer (i.e., the drug layer), with the second layer (sweller layer) containing a more viscous grade of polymer. In some embodiments, in conjunction with other above or below embodiments, the bilayer is coated with a semi-permeable membrane comprising a delivery port. In some embodiments, in conjunction with other above or below embodiments, the release rate of the drug is modulated by the uptake of water into the core of the tablet through the membrane, which results in swelling of the hydrophilic layers and resultant extrusion of the less viscous drug layer through the delivery port.

In some embodiments, in conjunction with other above or below embodiments, the formulation has a slower in-vitro release rate due to the slower rate (i.e. decreased permeability) of water uptake into the core, which is modulated by the coating composition and weight.

In some embodiments, in conjunction with other above or below embodiments, the exposure to omecamtiv mecarbil from two to twelve hours after dosing in humans is between 40 and 70 ng/ml. In some embodiments, in conjunction with other above or below embodiments, the exposure to omecamtiv mecarbil from two to twelve hours after dosing in humans is between 40 and 55 ng/ml.

In some embodiments, in conjunction with other above or below embodiments, the omecamtiv mecarbil is released in the following intervals:
≤30% dose dissolved at 1 hour;
30-75% dose dissolved at 3 hours; and
≥80% dose dissolved at 12 hours.

In some embodiments, in conjunction with other above or below embodiments, the omecamtiv mecarbil is released in the following intervals:
≤30% dose dissolved at 2 hours;
30-75% dose dissolved at 6 hours; and
≥80% dose dissolved at 16 hours.

Also provided is a pharmaceutical formulation comprising:
a drug layer comprising omecamtiv mecarbil, or a pharmaceutically acceptable salt, a pharmaceutically acceptable hydrate, or a pharmaceutically acceptable hydrate of a pharmaceutically acceptable salt thereof;
a sweller layer; and
a semi-permeable membrane coating having at least one delivery port.

Also provided is a pharmaceutical formulation comprising:
a drug layer comprising:
omecamtiv mecarbil, or a pharmaceutically acceptable salt, a pharmaceutically acceptable hydrate, or a pharmaceutically acceptable hydrate of a pharmaceutically acceptable salt thereof;
a drug layer polymer; and
a lubricant;
a sweller layer comprising:
a sweller layer polymer;
an osmotic agent;
a diluent; and
a lubricant; and
a semi-permeable membrane coating having at least one delivery port comprising:
an insoluble polymer; and
a pore forming polymer.

Also provided is a pharmaceutical formulation comprising:
a drug layer comprising:
omecamtiv mecarbil dihydrochloride hydrate;
a drug layer polymer; and
a lubricant;
a sweller layer comprising:
a sweller layer polymer;
an osmotic agent;
a diluent;
and a lubricant; and
a semi-permeable membrane coating having at least one delivery port comprising:
an insoluble polymer; and
a pore forming polymer.

In some embodiments, in conjunction with other above or below embodiments, the pharmaceutical formulation comprises:
a drug layer comprising: 10-20 (w/w %) omecamtiv mecarbil, or a pharmaceutically acceptable salt, a pharmaceutically acceptable hydrate, or a pharmaceutically acceptable hydrate of a pharmaceutically acceptable salt thereof; 40-60 (w/w %) polyethylene oxide; and 0-2% (w/w %) lubricant;
a sweller layer comprising: 12-30 (w/w %) polyethylene oxide; 2-10 (w/w %) an osmotic agent; 1-8 (w/w %) microcrystalline cellulose; and 0.1-2 (w/w %) lubricant; and
a semi-permeable membrane having at least one delivery port comprising: 5-15 (w/w %) cellulose acetate; 0.3-5 (w/w %) polyethylene glycol.

In some embodiments, in conjunction with other above or below embodiments, the pharmaceutical formulation comprises:
a drug layer comprising: 14-17 (w/w %) omecamtiv mecarbil dihydrochloride hydrate; 48-55 (w/w %) polyethylene oxide; and 0.1-0.5% (w/w %) lubricant;
a sweller layer comprising: 18-25 (w/w %) polyethylene oxide; 4-9 (w/w %) an osmotic agent; 3-6 (w/w %) microcrystalline cellulose; and 0.1-0.5 (w/w %) lubricant; and
a semi-permeable membrane having at least one delivery port comprising: 8-10 (w/w %) cellulose acetate; 0.5-3 (w/w %) polyethylene glycol.

In some embodiments, in conjunction with other above or below embodiments, the pharmaceutical formulation comprises:
a drug layer comprising: 10-20 (w/w %) omecamtiv mecarbil dihydrochloride hydrate; 40-60 (w/w %) polyethylene oxide; and 0-2% (w/w %) magnesium stearate;
a sweller layer comprising: 12-30 (w/w %) polyethylene oxide; 2-10 (w/w %) sodium chloride; 1-8 (w/w %) microcrystalline cellulose; and 0.1-2 (w/w %) magnesium stearate; and
a semi-permeable membrane having at least one delivery port comprising: 5-15 (w/w %) cellulose acetate; 0.3-5 (w/w %) polyethylene glycol 3350.

In some embodiments, in conjunction with other above or below embodiments, the pharmaceutical formulation comprises:
a drug layer comprising: 15-16 (w/w %) omecamtiv mecarbil dihydrochloride hydrate; 50-52 (w/w %) PolyOx™ WSR N-80; and 0.1-0.5% (w/w %) magnesium stearate;
a sweller layer comprising: 20-23 (w/w %) PolyOx™ WSR Coagulant; 4-9 (w/w %) sodium chloride; 3-6 (w/w %) Avicel PH 200; and 0.1-0.5 (w/w %) lubricant; and
a semi-permeable membrane having at least one delivery port comprising: 8-10 (w/w %) cellulose acetate; 0.5-3 (w/w %) polyethylene glycol 3350.

In some embodiments, in conjunction with other above or below embodiments, the pharmaceutical formulation comprises:
a drug layer comprising: 15-16 (w/w %) omecamtiv mecarbil dihydrochloride hydrate; 50-52 (w/w %) PolyOx™ WSR N-80; and 0.1-0.5% (w/w %) magnesium stearate;
a sweller layer comprising: 20-23 (w/w %) PolyOx™ WSR Coagulant; 4-9 (w/w %) sodium chloride; 3-6 (w/w %) Avicel PH 200; and 0.1-0.5 (w/w %) lubricant; and
a semi-permeable membrane having at least one delivery port comprising: 8-9 (w/w %) cellulose acetate; 2-3 (w/w %) polyethylene glycol 3350.

In some embodiments, in conjunction with other above or below embodiments, the pharmaceutical formulation comprises:
a drug layer comprising: 15-16 (w/w %) omecamtiv mecarbil dihydrochloride hydrate; 50-52 (w/w %) PolyOx™ WSR N-80; and 0.1-0.5% (w/w %) magnesium stearate;
a sweller layer comprising: 20-23 (w/w %) PolyOx™ WSR Coagulant; 4-9 (w/w %) sodium chloride; 3-6 (w/w %) Avicel PH 200; and 0.1-0.5 (w/w %) lubricant; and a semi-permeable membrane having at least one delivery port comprising: 9-10 (w/w %) cellulose acetate; 0.5-2 (w/w %) polyethylene glycol 3350.

Omecamtiv Mecarbil

In some embodiments, in conjunction with other above or below embodiments, the drug formulation comprises omecamtiv mecarbil dihydrochloride salt. In some embodiments, in conjunction with other above or below embodiments, the drug formulation comprises omecamtiv mecarbil dihydrochloride hydrate. In some embodiments, in conjunction with other above or below embodiments, the drug formulation comprises omecamtiv mecarbil dihydrochloride hydrate Form A.

Figure 5:
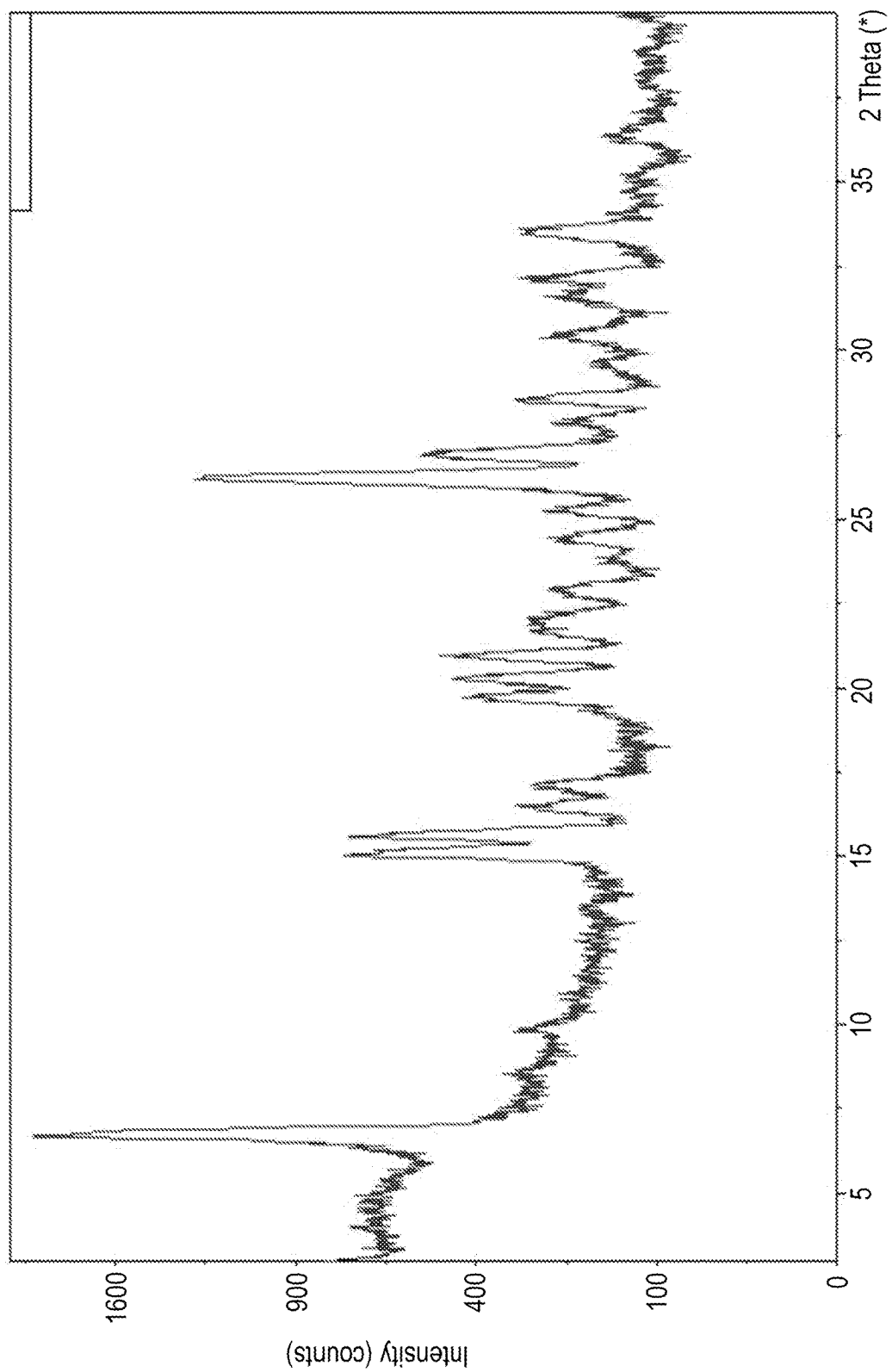
FIG. 5 shows an X-ray powder diffraction pattern (XRPD) for Form A.

In some embodiments, in conjunction with other above or below embodiments, Form A can be characterized by an X-ray powder diffraction pattern, obtained as set forth in the Examples, having peaks at about 6.6, 14.9, 20.1, 21.4, and 26.8±0.2° 2θ using Cu Kα radiation. Form A optionally can be further characterized by an X-ray powder diffraction pattern having additional peaks at about 8.4, 24.2, 26.0, 33.3±0.2° 2θ using Cu Kα radiation. Form A optionally can be even further characterized by an X-ray powder diffraction pattern having additional peaks at about 6.2, 9.7, 13.2, 14.3, 15.4, 16.3, 16.9, 18.9, 19.5, 20.7, 21.8, 22.8, 23.6, 25.1, 27.3, 27.7, 28.4, 29.4, 30.2, 31.2, 31.5, 31.9, 33.9, 34.5, 34.9, 36.1, 36.8, 37.7, 38.5, and 39.7±0.2° 2θ using Cu Kα radiation. In various cases, Form A can be characterized by an XRPD pattern having peaks at about 6.2, 6.6, 8.4, 9.7, 13.2, 14.3, 14.9, 15.4, 16.3, 16.9, 18.9, 19.5, 20.1, 20.7, 21.4, 21.8, 22.8, 23.6, 24.3, 25.1, 26.0, 26.8, 27.3, 27.7, 28.4, 29.4, 30.2, 31.2, 31.5, 31.9, 33.3, 33.9, 34.5, 34.9, 36.1, 36.8, 37.7, 38.5, and 39.7±0.2° 2θ using Cu Kα radiation. In some embodiments, in conjunction with other above or below embodiments, Form A can be characterized by an X-ray powder diffraction pattern substantially as depicted in FIG. 5. It is well known in the field of XRPD that while relative peak heights in spectra are dependent on a number of factors, such as sample preparation and instrument geometry, peak positions are relatively insensitive to experimental details.

Figure 6:
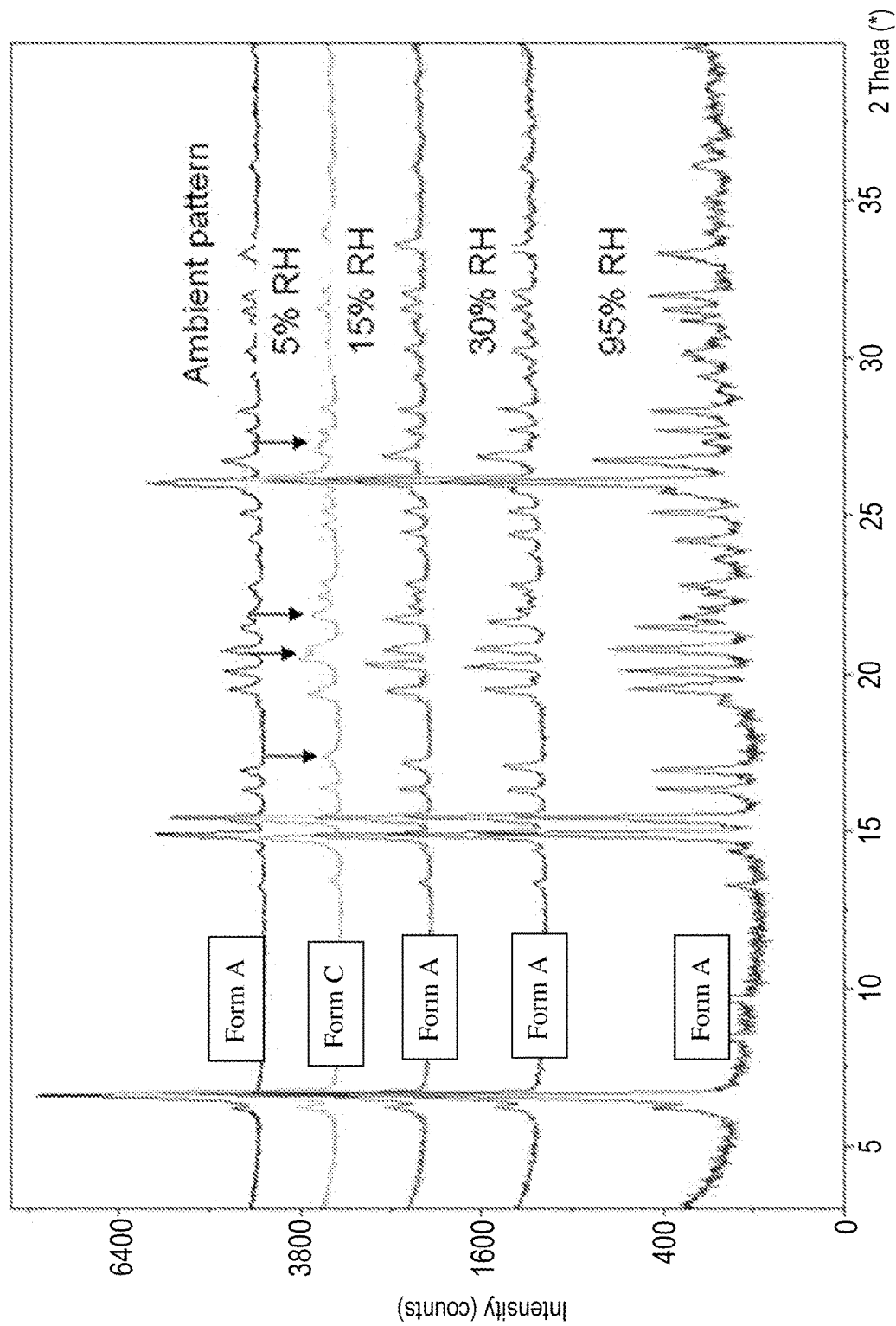
FIG. 6 shows an X-ray powder diffraction pattern (XRPD) of a omecamtiv mecarbil dihydrochloride hydrate salt form at varying relative humidity conditions.

Form B and Form C polymorphs of omecamtiv mecarbil, are metastable anhydrous dihydrochloride forms, and can be formed under varied hydration conditions, as noted in FIG. 6. Characteristic Form B 2-theta values include 6.8, 8.8, 14.7, 17.7, and 22.3±0.2° 2θ using Cu Kα radiation, and can additionally include peaks at 9.6, 13.5, 19.2, 26.2±0.2° 2θ using Cu Kα radiation. Form B can be characterized with XRPD pattern peaks at 6.2, 6.8, 8.8, 9.6, 13.5, 14.4, 14.7, 15.4, 16.3, 17.0, 17.7, 18.3, 19.2, 19.9, 20.5, 20.8, 21.8, 22.3, 22.7, 23.0, 24.8, 25.1, 25.5, 26.2, 26.4, 26.8, 27.5, 28.5, 30.2, 30.6, 31.1, 31.5, 32.1, 32.7, 34.1, 34.4, 35.5, 35.9, 38.1, 38.9±0.2° 2θ using Cu Kα radiation. Characteristic Form C 2-theta values include 6.7, 14.8, 17.4, 20.6, and 26.2±0.2° 2θ using Cu Kα radiation, and can additionally include peaks at 8.7, 22.0, 27.1, and 27.7±0.2° 2θ using Cu Kα radiation. Form C can be characterized with XRPD pattern peaks at 6.2, 6.7, 8.7, 9.6, 13.5, 14.5, 14.8, 15.4, 16.4, 17.1, 17.4, 18.4, 19.3, 19.5, 19.9, 20.6, 20.8, 21.8, 22.0, 22.5, 22.8, 24.3, 24.7, 25.1, 25.6, 26.2, 26.5, 27.1, 27.3, 27.7, 28.5, 30.0, 30.5, 31.0, 31.5, 32.2, 32.8, 34.1, 35.2, 36.0, 36.9, and 38.8±0.2° 2θ using Cu Kα radiation.

Figure 7:
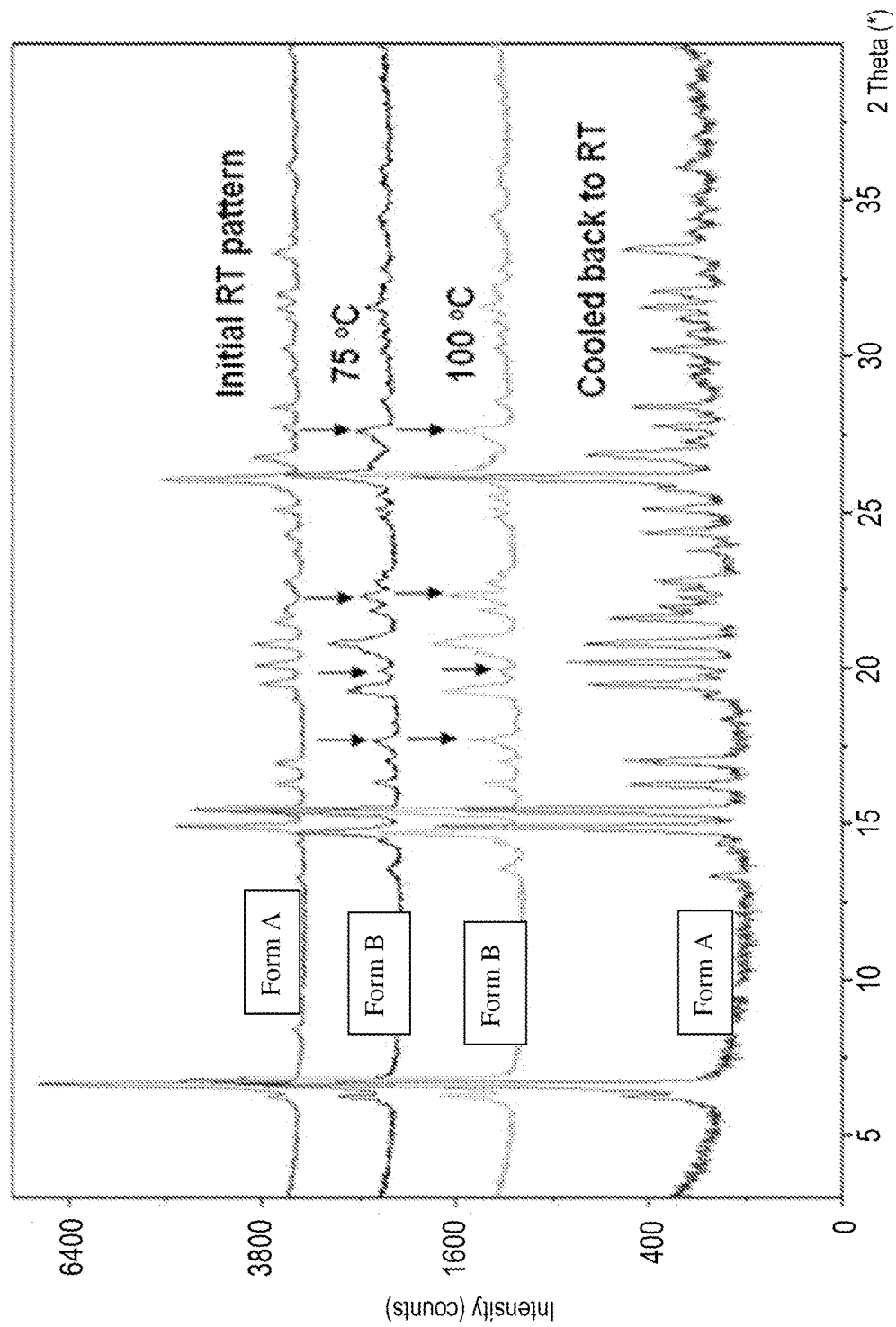
FIG. 7 shows an X-ray powder diffraction pattern (XRPD) of a omecamtiv mecarbil dihydrochloride hydrate salt form at varying temperatures.
Figure 8:
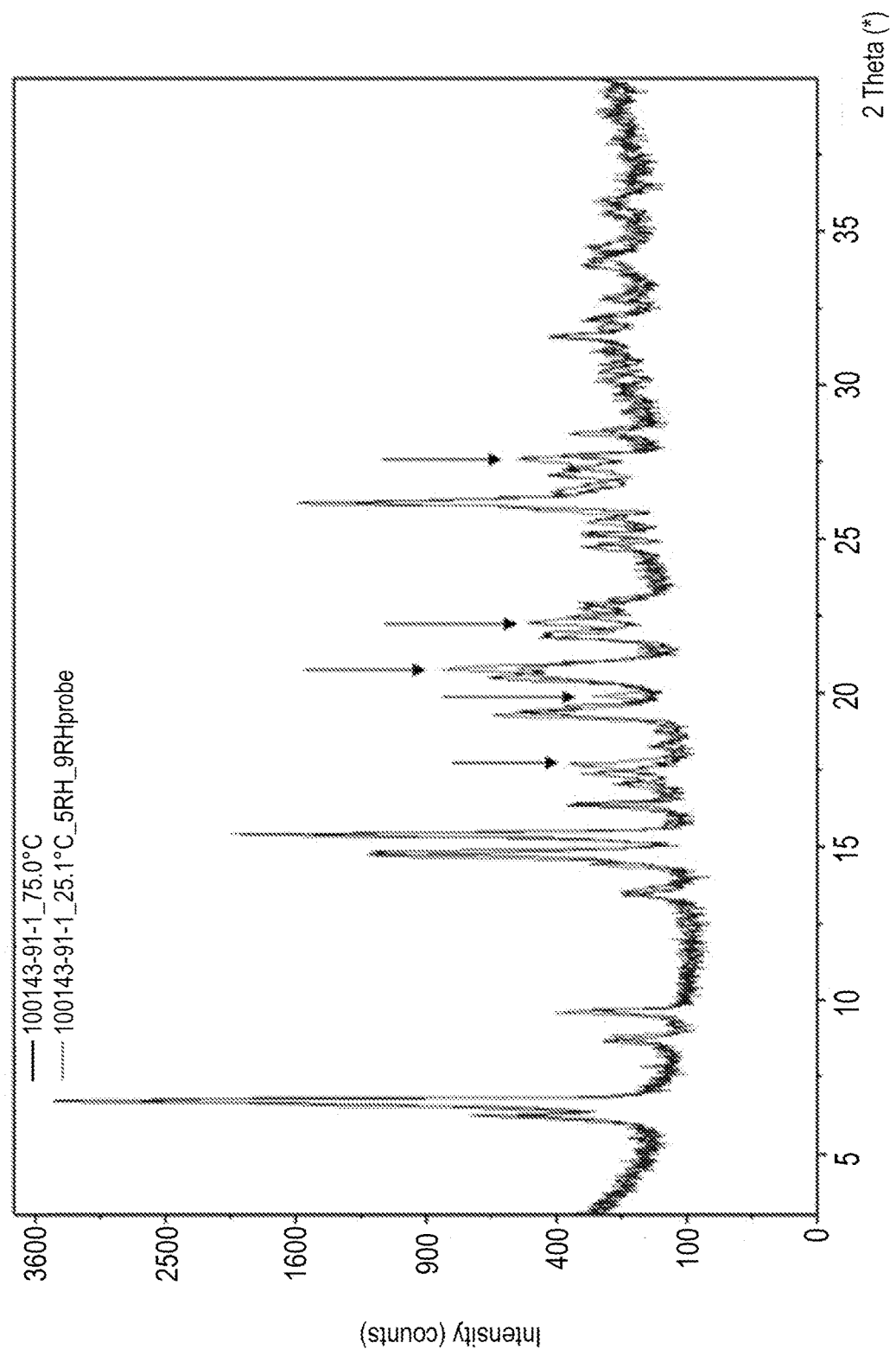
FIG. 8 shows an overlay of XRPD patterns for Forms A, B and C of omecamtiv mecarbil dihydrochloride salt.

See, also, FIG. 7 (variable temperature XRPD data), FIG. 6 (variable relative humidity XRPD data), and FIG. 8 (overlay).

The Drug Layer Polymer

The drug layer polymer generally is a material that has high water solubility and in operation forms aqueous solutions with viscosities of at least 50 centipoise (cp) and, in some embodiments, in conjunction with other above or below embodiments, aqueous solutions with viscosities of 200 cp or greater.

The drug layer polymer may be a single material or a mixture of materials. Examples of such materials include polyols, and oligomers of polyethers, such as ethylene glycol oligomers or propylene glycol oligomers. In addition, mixtures of polyfunctional organic acids and cationic materials such as amino acids or multivalent salts, such as calcium salts may be used. In some embodiments, in conjunction with other above or below embodiments, the drug layer polymer ispolyethylene oxide (PEO), polyvinyl alcohol, PVP, cellulosics such as hydroxyethyl cellulose (HEC), hydroxypropylcellulose (HPC), HPMC, methyl cellulose (MC), carboxy methyl cellulose (CMC), carboxyethyl¬ cellulose (CEC), gelatin, xanthan gum or any other water-soluble polymer that forms an aqueous solution with a viscosity similar to that of the polymers listed above.

In some embodiments, in conjunction with other above or below embodiments, the drug layer polymer comprises polyethylene oxide (PEO).

In some embodiments, in conjunction with other above or below embodiments, the drug layer polymer is noncross-linked PEO or mixtures of PEO with the other materials listed above.

In some embodiments, in conjunction with other above or below embodiments, the drug layer polymer is Polyethylene Oxide N-80.

In some embodiments, in conjunction with other above or below embodiments, the drug layer polymer is PolyOx WSR N-80.

The amount of the drug layer polymer present in the drug layer may range from about 20 wt % to about 98 wt % of the drug-containing composition.

Lubricants

Lubricants include stearic acid, hydrogenated vegetable oils, hydrogenated soybean oil and hydrogenated soybean oil & castor wax, stearyl alcohol, leucine, polyethylene glycol, magnesium stearate, glyceryl monostearate, stearic acid, glycerybehenate, polyethylene glycol, ethylene oxide polymers, sodium lauryl sulfate, magnesium lauryl sulfate, sodium oleate, sodium stearyl Fumarate, DL-leucine, colloidal silica, and mixtures thereof.

In some embodiments, in conjunction with other above or below embodiments, the lubricant is selected from magnesium stearate.

Other Excipients

The drug layer may also include other conventional excipients, such as those that promote performance, tableting or processing of the dosage form. Such excipients include diluents, surfactants, water-soluble polymers, pH modifiers, fillers, binders, pigments, osmagents, disintegrants and lubricants. Exemplary excipients include microcrystalline cellulose; metallic salts of acids such as aluminum stearate, calcium stearate, magnesium stearate, sodium stearate, and zinc stearate; fatty acids, hydrocarbons and fatty alcohols such as stearic acid, palmitic acid, liquid paraffin, stearyl alcohol, and palmitol; fatty acid esters such as glyceryl (mono- and di-) stearates, triglycerides, glyceryl (palmitic stearic) ester, sorbitan monostearate, saccharose monostearate, saccharose monopalmitate, and sodium stearyl fumarate; alkyl sulfates such as sodium lauryl sulfate and magnesium lauryl sulfate; polymers such as polyethylene glycols, polyoxyethylene glycols, and polytetrafluoroethylene; and inorganic materials such as talc and dicalcium phosphate.

The Sweller Layer

The sweller layer expands as it imbibes water through the coating from the use environment. As it expands, the sweller layer increases the pressure within the core, causing extrusion of the drug layer through a delivery port(s) into the environment of use.

The degree of swelling of the sweller layer itself can be assessed by measuring its swelling ratio. In some embodiments, in conjunction with other above or below embodiments, the sweller layer has a swelling ratio of at least about 2.

In some embodiments, in conjunction with other above or below embodiments, the mass ratio of drug layer to sweller layer is about 2 to 1.

In some embodiments, in conjunction with other above or below embodiments, the sweller layer comprises: a sweller layer polymer; an osmotic agent; a diluent; and a lubricant.

A. Sweller Layer Polymer

The sweller layer polymer is generally a water-swellable polymer that expands in the presence of water. The degree of swelling of a sweller layer polymer can be assessed by measuring its swelling ratio. Suitable sweller layer polymers for the sweller layer are generally hydrophilic polymers that have swelling ratios of at least about 2.0.

In general, the molecular weight of polymers chosen for the sweller layer polymer is higher than that of similar polymers used as drug layer polymers such that, at a given time during drug release, the sweller layer, after imbibing water tends to be more viscous, less fluid, and more elastic relative to the drug layer. In some cases the sweller layer polymer may be even substantially or almost entirely water insoluble, such that when partially water swollen during operation, it may constitute a mass of water-swollen elastic particles.

Exemplary sweller layer polymer include polyoxomers such as PEO, cellulosics such as HPMC and HEC, and ionic polymers.

In some embodiments, in conjunction with other above or below embodiments, the sweller layer polymer comprises PEO with a molecular weight of about 800,000 daltons or more is used, for example, a molecular weight of 3,000,000 to 8,000,000 daltons.

In some embodiments, in conjunction with other above or below embodiments, the sweller layer polymer is selected from a polyethylene oxide.

In some embodiments, in conjunction with other above or below embodiments, the sweller layer polymer is PolyOx WSR coagulant In some embodiments, in conjunction with other above or below embodiments, the sweller layer comprises a sweller layer polymer in an amount ranging from about 30 to 100 wt % of the sweller layer.

B. Osmotic Agent

The sweller layer comprises an osmotic agent to facilitate water uptake into the layer.

Osmotic agents include sodium chloride, glycine, citric acid, disodium hydrogen phosphate, lactose, mannitol, sorbitol, glucose, sucrose, and fructose and mixtures thereof.

In some embodiments, in conjunction with other above or below embodiments, the osmotic agent is selected from sodium chloride.

C. Diluent

The sweller layer comprises a diluent. In some embodiments, in conjunction with other above or below embodiments, the diluent is present in an amount of 5 to 50 wt % of the sweller layer.

In general, the diluent is a hydrophilic materials with good compression properties. Exemplary diluents include sugars such as lactose, in particular spray-dried versions sold under the trade name FASTFLOW LACTOSE, or xylitol, polymers such as microcrystalline cellulose, HPC, MC or HPMC. In some embodiments, in conjunction with other above or below embodiments, diluents are microcrystalline cellulose, both standard grades sold under the trade name AVI CEL and silicified versions sold under the trade name PROSOLV and HPC. In some embodiments, in conjunction with other above or below embodiments, the diluent is selected from microcrystalline cellulose.

In some embodiments, in conjunction with other above or below embodiments, the diluent is Avicel PH 200.

The amount of diluent is chosen to be sufficiently high so that the core compresses well yet sufficiently low so that the sweller layer still has a swelling ratio of at least 2. Typically, the amount is at least 20 but less than 60 wt %.

D. Pigment

In some embodiments, in conjunction with other above or below embodiments, the sweller layer also includes a pigment, which may, e.g., facilitate side selection during delivery port drilling. In some embodiments, in conjunction with other above or below embodiments, the pigment is selected from Alu Lake. In some embodiments, in conjunction with other above or below embodiments, the pigment is selected from FD&C Blue#2 Lake (E132).

In some embodiments, in conjunction with other above or below embodiments, the pigment is present in an amount of 0.1-2 (w/w %), such as 0.1-0.5 (w/w %).

E. Other Excipients

The sweller layer may also include solubility-enhancing agents or excipients that promote stability, tableting or processing of the dosage form of the same types mentioned above in connection with the drug layer. However, generally such excipients comprise a minor portion of the sweller layer. In some embodiments, in conjunction with other above or below embodiments, the sweller layer contains a lubricant such as magnesium stearate.

Semi-Permeable Membrane Coating

The semi-permeable membrane coating is chosen to control the rate at which water enters the core, thus controlling, at least in part, the rate at which drug is delivered to the use environment. In some embodiments, in conjunction with other above or below embodiments, a high permeability coating is used to achieve the desired drug release profile while keeping the tablet acceptably small. High strength ensures the coating does not burst when the core swells as it imbibes water, leading to an uncontrolled delivery of the core contents to the use environment.

Furthermore, the semi-permeable membrane coating is non-dissolving and non-eroding during release of the drug-containing composition, generally meaning that the semi-permeable membrane coating is sufficiently water-insoluble that drug is substantially entirely delivered through the delivery port(s), in contrast to delivery via permeation through coating.

In some embodiments, in conjunction with other above or below embodiments, the semi-permeable membrane coating comprises: an insoluble polymer coating; and a pore forming polymer.

Insoluble Polymer Coating

In some embodiments, in conjunction with other above or below embodiments, the insoluble polymer coating comprises plasticized or unplasticized cellulose esters, ethers, and ester-ethers. In some embodiments, in conjunction with other above or below embodiments, suitable insoluble polymers include cellulose acetate ("CA"), cellulose acetate butyrate, and ethyl cellulose.

In some embodiments, in conjunction with other above or below embodiments, the insoluble polymer coating is a cellulose acetate having acetyl contents of 25 to 42%.

In some embodiments, in conjunction with other above or below embodiments, the insoluble polymer coating is selected from cellulose acetate.

In some embodiments, in conjunction with other above or below embodiments, insoluble polymer coating is cellulose acetate CA-398-10.

Pore Forming Polymer

The semi-permeable membrane coating may also comprise a pore forming polymer in any amount so long as the polymer remains substantially soluble at the conditions used to form the coating and so long as the coating remains water-permeable and has sufficient strength. Pore forming polymers and their use in fabricating coatings are described in U.S. Pat. Nos. 5,612,059 and 5,698,220, the pertinent disclosures of which are incorporated herein. The term "pore forming polymer," as used herein, refers to a material added to the coating solution that has low or no volatility relative to the solvent such that it remains as part of the coating following the coating process, but that is sufficiently water swellable or water soluble such that, in the aqueous use environment it provides a water-filled or water-swollen channel or pore to allow the passage of water thereby enhancing the water permeability of the coating.

Suitable pore forming polymers include polyethylene glycol (PEG), PVP, PEO, HEC, HPMC and other aqueous-soluble cellulosics, polyacrylic acid and various copolymers and mixtures of these water soluble or water swellable polymers. Enteric polymers such as cellulose acetate phthalate (CAP) and HPMCAS are included in this class of polymers. In some embodiments, in conjunction with other above or below embodiments, the pore forming polymer is PEG having an average molecular weight from 1000 to 8000 daltons. In some embodiments, in conjunction with other above or below embodiments, the weight ratio of CA:PEG should range from about 6.5:3.5 to about 9:1.

In some embodiments, in conjunction with other above or below embodiments, the pore former is polyethylene gylcol 3350.

In some embodiments, in conjunction with other above or below embodiments, the pore former is Carbowax® 3350.

In some embodiments, in conjunction with other above or below embodiments, the semi-permeable membrane coating comprises 90% insoluble polymer coating and 10% pore forming polymers.

In some embodiments, in conjunction with other above or below embodiments, the semi-permeable membrane coating comprises 90% CA and 10% PEG.

In some embodiments, in conjunction with other above or below embodiments, the semi-permeable membrane coating comprises 80% insoluble polymer coating and 20% pore forming polymers.

In some embodiments, in conjunction with other above or below embodiments, the semi-permeable membrane coating comprises 80% CA and 20% PEG.

Delivery Port

The coating contains at least one delivery port in communication with the interior and exterior of the coating to allow for release of the drug-containing composition to the exterior of the dosage form. The delivery port can range in size from about the size of the drug particles, and thus could be as small as 1 to 100 microns in diameter and may be termed pores, up to about 5000 microns in diameter. The shape of the port may be substantially circular, in the form of a slit, or other convenient shape to ease manufacturing and processing. The port(s) may be formed by postcoating mechanical or thermal means or with a beam of light (e.g., a laser), a beam of particles, or other high-energy source, or may be formed in situ by rupture of a small portion of the coating. Such rupture may be controlled by intentionally incorporating a relatively small weak portion into the coating. Delivery ports may also be formed in situ by erosion of a plug of water-soluble material or by rupture of a thinner portion of the coating over an indentation in the core. Delivery ports may be formed by coating the core such that one or more small regions remains uncoated. In addition, the delivery port can be a large number of holes or pores that may be formed during coating, as in the case of asymmetric membrane coatings of the type disclosed in U.S. Pat. Nos. 5,612,059 and 5,698,220, the disclosures of which are incorporated by reference. When the delivery pathways are pores there can be a multitude of such pores that range in size from 1 μm to greater than 100 μm. During operation, one or more of such pores may enlarge under the influence of the hydrostatic pressure generated during operation. The number of delivery ports may vary from 1 to 10 or more. At least one delivery port should be formed on the side of the drug layer, so that the drug layer will be extruded out of the delivery port by the swelling action of the sweller layer. In aggregate, the total surface area of core exposed by delivery ports is less than 5%, and more typically less than 1%.

Methods of Preparation

Also provided is a process for the preparation of the pharmaceutical formulations described herein. In some embodiments, in conjunction with other above or below embodiments, the process comprises:

providing a bilayer core tablet comprising
a drug layer comprising omecamtiv mecarbil, or a pharmaceutically acceptable salt, a pharmaceutically acceptable hydrate, or a pharmaceutically acceptable hydrate of a pharmaceutically acceptable salt thereof; and
a sweller layer;
applying a semi-permeable coating to the bilayer core tablet; and
forming at least one delivery port in said semi-permeable coating.

In some embodiments, in conjunction with other above or below embodiments, the bilayer core tablet is prepared by a process comprising:

providing a drug layer blend comprising omecamtiv mecarbil, or a pharmaceutically acceptable salt, a pharmaceutically acceptable hydrate, or a pharmaceutically acceptable hydrate of a pharmaceutically acceptable salt thereof; and
providing a sweller layer blend comprising a sweller layer polymer; an osmotic agent; a diluent; and a lubricant; and
compressing the drug layer blend and the sweller layer blend to form the bilayer core tablet.

Methods of Use

Also provided is a method for the use of such pharmaceutical formulations for the treatment of heart failure, including but not limited to: acute (or decompensated)

congestive heart failure, and chronic congestive heart failure; particularly diseases associated with systolic heart dysfunction.

EXAMPLES

Reagents and solvents were used as received from commercial sources. $^1$H NMR spectra were recorded on a 400 MHz spectrometer. Chemical shifts are reported in ppm from tetramethylsilane with the solvent resonance as the internal standard (CDCl$_3$, DMSO-d$_6$). Data are reported as follows: chemical shift, multiplicity (s=singlet, d=doublet, t=triplet, q=quartet, br=broad, m=multiplet), coupling constants (Hz) and integration. $^{13}$C NMR spectra were recorded on a 100 MHz spectrometer with complete proton decoupling. Chemical shifts are reported in ppm from tetramethylsilane with the solvent as the internal reference (CDCl$_3$, DMSO-d$_6$). All solvent charges are made with respect to starting 2-Fluoro-3-nitrotoluene. X-Ray powder diffraction data (XRPD) were obtained using a PANalyticalX'Pert PRO diffractometer (PANalytical, Almelo, The Netherlands) fitted with a real time multiple strip (RTMS) detector. The radiation used was CuKα (1.54 Å) and the voltage and current were set at 45 kV and 40 mA, respectively. Data were collected at room temperature from 5 to 45 degrees 2-theta with a step size of 0.0334 degrees. Samples were prepared on a low background sample holder and placed on the sample stage which was rotated with a 2 second revolution time.

Alternatively, XRPD data were obtained using a PANalyticalX'Pert PRO diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 5 to 40, degrees 2-theta with a step size of 0.0334 degrees. Samples were prepared on a low background sample holder and placed on the sample stage which was rotated with a 2 second revolution time.

Alternatively, XRPD data were obtained using a PANalyticalX'Pert PRO diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 5 to 40, degrees 2-theta with a step size of 0.0167 degrees. Samples were prepared on a low background sample holder and placed on the sample stage which was rotated with a 2 second revolution time.

Alternatively, XRPD data were obtained using a PANalyticalX'Pert Pro diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 3 to 40, degrees 2-theta with a step size of 0.008 degrees. Samples were prepared on a low background sample holder and placed on the sample stage with a 2 second revolution time.

Alternatively, XRPD data were obtained using a Bruker D8 Discover X-ray diffraction system (Bruker, Billerica, Mass.) fitted with a motorized xyz sample stage and a GADDS area detector. The radiation used was CuKα (1.54 Å) and the voltage and current were set at 45 kV and 40 mA, respectively. The solid samples on a flat glass plate were mapped and for each sample an area of 1 mm$^2$ was scanned in an oscillating mode for 3 minutes from 5 to 48 degrees 2-theta.

Differential Scanning calorimetry (DSC) data was collected using standard DSC mode (DSC Q200, TA Instruments, New Castle, Del.). A heating rate of 10° C./min was employed over a temperature range from 40° C. to 300° C. Analysis was run under nitrogen and samples were loaded in standard, hermetically-sealed aluminum pans. Indium was used as a calibration standard.

Alternatively, DSC data were collected using temperature-modulated DSC mode (DSC Q200, TA Instruments, New Castle, Del.). After sample equilibration at 20° C. for five minutes, the heating rate of 3° C./min was employed with a modulation of +/−0.75° C./min over a temperature range from 20° C. to 200° C. Analysis was run under nitrogen and samples were loaded in standard, uncrimped aluminum pans. Indium was used as a calibration standard.

Manufacture of Omecamtiv Mecarbil Dihydrochloride Hydrate Synthetic Route to Omecamtiv Mecarbil

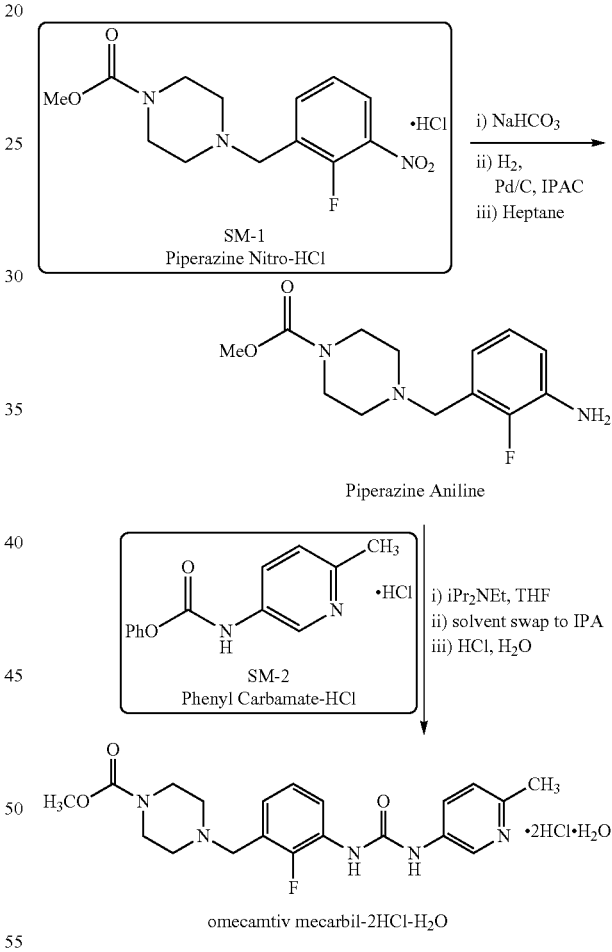

Synthesis of the API SM Piperazine Nitro-HCl

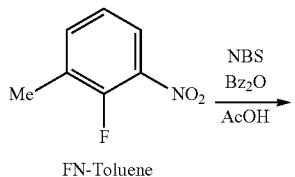

FN-Toluene

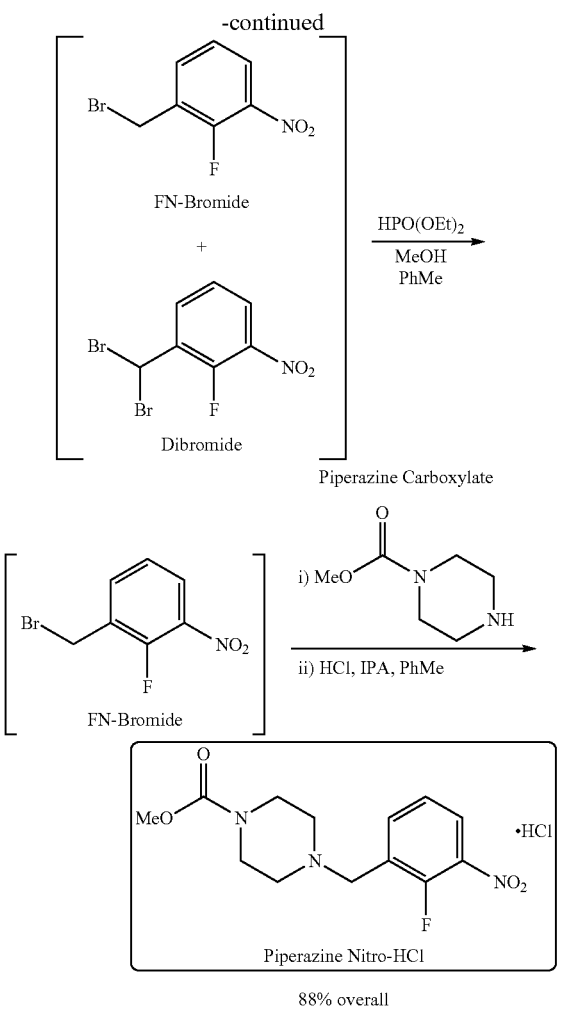

88% overall

FN-Bromide

In a 60 L reactor (containing no exposed Stainless steel, Hastelloy®, or other metal parts) equipped with a reflux/return condenser and scrubber charged with a 5N NaOH solution, a mechanically stirred mixture of FN-Toluene (2.0 kg, 12.89 mol, 1.0 equiv.), N-Bromosuccinimide (3.9 kg, 21.92 mol, 1.70 equiv.), benzoyl peroxide (125.0 g, 0.03 equiv., 0.39 mol, containing 25 wt % water), and acetic acid (7.0 L, 3.5 volumes) was heated to 85° C. under an atmosphere of nitrogen for 7 hours. A solution of $H_3PO_3$ (106.0 g, 1.29 mol, 0.1 equiv.) and acetic acid (200 mL, 0.1 volume), prepared in separate vessel, was added. The reaction mixture was agitated for 0.5 h and analysis of an aliquot confirmed complete decomposition of benzoyl peroxide (not detected, $HPLC_{254\ nm}$). The reaction mixture was cooled to 22° C. DI Water (8.0 L, 4 volumes) and toluene (16.0 L, 8 volumes) were charged, the biphasic mixture was agitated (20 min), and the layers were separated. Aqueous 1.6N NaOH (14.0 L, 7.0 volumes) was added to the organic layer at a rate allowing the batch temperature to stay under 25° C. and the pH of the resultant aqueous phase was measured (≥11). The biphasic mixture was filtered through a 5 μm Teflon® cartridge line and the layers were separated. The filter line was washed with another 2 L of toluene.

The assay yields were 2.5% of FN-Toluene, 62.3% of FN-Bromide and 30.0% of Di-Bromide. The toluene solution contained no benzoyl peroxide, succinimide, or α-bromoacetic acid and water content by KF titration was 1030 ppm (This solution could be held under nitrogen at room temperature for >12 h without any change in the assay yield).

To this solution at room temperature was added diisopropylethylamine (880.0 g, 6.63 mol, 0.53 equiv.) followed by methanol (460 mL, 11.28 mol, 0.88 equiv.) and heated to 40° C. A solution of diethylphosphite (820.0 g, 5.63 mol, 0.46 equiv.) in methanol (460 mL, 11.28 mol, 0.88 equiv.) was prepared and added to the reaction mixture at 40° C. through an addition funnel over a period of 1 hour at such a rate that the batch temperature was within 40±5° C. The contents were stirred for a period of 3 h at 40° C. from the start of addition and cooled to room temperature and held under nitrogen atmosphere for 12 hours. The assay yield of the reaction mixture was 2.5% FN-Toluene 92.0% FN-Bromide and 0.2% Di-Bromide. This solution is used as such for the alkylation step.

Characterization for components of final product mixture (collected for pure compounds).

2-Fluoro-3-Nitrotoluene (FN-Toluene): $^1H$ NMR (400 MHz, CHLOROFORM-d) δ ppm 2.37 (s, 1H), 7.13-7.20 (m, 1H), 7.45-7.51 (m, 1H), 7.79-7.85 (m, 1H). $^{13}C$ NMR (100 MHz, CHLOROFORM-d) δ ppm 14.3 (d, J=5 Hz), 123.3 (d, J=3 Hz), 123.6 (d, J=5 Hz), 128.2 (d, J=16 Hz), 136.7 (d, J=5 Hz), 137.5 (broad), 153.7 (d, J=261 Hz); 1-(bromomethyl)-2-fluoro-3-nitrobenzene (FN-Bromide): $^1H$ NMR (400 MHz, CHLOROFORM-d) δ ppm 4.56 (s, 1H), 7.28-7.34 (m, 1H), 7.69-7.76 (m, 1H), 7.98-8.05 (m, 1H). $^{13}C$ NMR (100 MHz, CHLOROFORM-d) δ ppm 23.6 (d, J=5 Hz), 124.5 (d, J=5 Hz), 126.1 (d, J=3 Hz), 128.5 (d, J=14 Hz), 136.5 (d, J=4 Hz), 137.7 (broad), 153.3 (d, J=265 Hz). DSC: single melt at 53.59° C. Exact Mass $[C_7H_5BrFNO_2+H]^+$: calc.=233.9566, measured=233.9561; 1-(dibromomethyl)-2-fluoro-3-nitrobenzene (Dibromide): $^1H$ NMR (400 MHz, CHLOROFORM-d) δ ppm 6.97 (s, 1H), 7.39-7.45 (m, 1H), 8.03-8.10 (m, 1H), 8.16-8.21 (m, 1H). $^{13}C$ NMR (100 MHz, CHLOROFORM-d) δ ppm 29.2 (d, J=7 Hz), 124.9 (d, J=5 Hz), 127.1 (d, J=2 Hz), 132.1 (d, J=11 Hz), 135.7 (d, J=2 Hz), 137.2 (broad), 149.8 (d, J=266 Hz). DSC: single melt at 49.03° C. Exact Mass $[C_7H_4Br_2FNO_2+H]^+$: calc.=311.8671, measured=311.8666.

Piperazine Nitro-HCl:

To a mechanically stirred toluene solution (9 volumes) of FN-Bromide (prepared from previous step) in a 60 L reactor at 22° C. under an atmosphere of nitrogen, diisopropylethylamine was charged (1.90 kg, 14.69 mol, 1.14 equiv.). To this mixture a solution of piperazine carboxylate methylester (Piperazine Carboxylate) (2.03 kg, 14.05 mol, 1.09 equiv.) in toluene (1.0 L, 0.5 volumes) was added at a rate allowing the batch temperature to stay under 30.0° C. (Exothermic. During the addition, jacket temperature was adjusted to 5° C. in order to maintain batch temperature below 30° C. The mixture was agitated at 22° C. for 3 hours and analysis of an aliquot confirmed completion of the alkylation reaction (<1.0 LCAP FN-Bromide, $HPLC_{254\ nm}$). The reaction mixture was treated with aqueous $NH_4Cl$ (20 wt %, 10.0 L, 5 volumes; prepared from 2.0 kg of $NH_4Cl$ and 10.0 L of DI water), the biphasic mixture was agitated (30 min), and the layers were separated. The organic layer was sequentially washed with aqueous $NaHCO_3$ (9 wt %, 10.0 L, 5 volumes; prepared from 0.90 kg of $NaHCO_3$ and 10.0 L of DI water). The organic layer was filtered through a 5 μm Teflon® cartridge line and transferred in a drum, washed the filter line with another 1.0 L toluene and the combined toluene solution (10.0 volumes) weighed, and assayed (HPLC) to quantify Piperazine Nitro free base. The assay yield for the Piperazine Nitro-freebase is 89.0%, FN-Toluene 2.5% and FN-Bromide 0.2% with FN-Bromide undetected. The total loss of product to the aqueous washes is <1.0%. This solution under nitrogen atmosphere is stable for more than 12 h.

To a mechanically stirred toluene solution of Piperazine Nitro free base, prepared as described above, at 22° C. in a 60 L reactor under an atmosphere of nitrogen, IPA (19.4 L, 9.7 volumes) and DI water (1.0 L, 0.5 volume) were charged. The mixture was heated to 55° C. and 20% of the 1.4 equiv. of conc. HCl (Titrated prior to use and charge based on titer value; 276.0 mL, 3.21 mol) was charged. The contents were agitated for 15 min and Piperazine Nitro-HCl seed (130.0 g, 0.39 mol, 0.03 equiv.) was charged as slurry in IPA (400 mL, 0.2 volume). The mixture was agitated for 30 min and the remaining conc. HCl (80% of the charge, 1.10 L, 12.82 mol) was added over a period of 4 hours. The mixture was stirred at 55° C. for 1 h, cooled to 20° C. in a linear manner over 1.5 hours, and agitated at this temperature for 12 hours. The supernatant concentration of Piperazine Nitro-HCl was measured (2.8 mg/g). The mixture was filtered through an aurora filter equipped with a 5 μm Teflon® cloth. The mother liquor were transferred to a clean drum and assayed. The filter cake was washed twice with IPA (11.2 L, 5.6 volumes) and dried to constant weight (defined as ≤1.0% weight loss for 2 consecutive TGA measurements over a period of 2 hours) on filter with vacuum and a nitrogen sweep (14 h). The combined losses of Piperazine Nitro-HCl in the mother liquors and the washes were 2.5%. Piperazine Nitro-HCl was isolated 3.59 kg in 87.6% corrected yield with >99.5 wt % and 99.0% LCAP purity.

Methyl 4-(2-fluoro-3-nitrobenzyl)piperazine-1-carboxylate hydrochloride (Piperazine Nitro-HCl): $^1$H NMR (300 MHz, DMSO-d) δ ppm 3.25 (br. s, 3H), 3.52-3.66 (m, 8H), 4.47 (s, 2H), 7.44-7.63 (t, 1H, J=8 Hz), 7.98-8.15 (m, 1H), 8.17-8.34 (m, 1H). $^{13}$C NMR (75 MHz, DMSO-d) δ ppm 50.3, 51.4, 52.8, 119.6 (d, J=14 Hz), 125.1 (d, J=5 Hz), 127.9, 137.4 (d, J=8 Hz), 139.8 (d, J=3 Hz), 152.2, 154.7, 155.7. DSC: melt onset at 248.4° C. Exact Mass $[C_{13}H_{16}FN_3O_4+H]^+$: calculated=298.1203, measured=298.1198.

Piperazine Nitro Freebase:

In a 60 L reactor equipped with a reflux/return condenser, a mixture of Piperazine Nitro-HCl (2.0 kg, 5.99 mol, 1.0 equiv.) and isopropyl acetate (6.0 L, 3.0 volumes) was mechanically agitated at ambient temperature under an atmosphere of nitrogen. A solution of sodium bicarbonate (629 g, 7.49 mol, 1.25 equiv.) and water (7.5 L, 3.75 volume), prepared in separate vessel, was added. The biphasic mixture was agitated (15 min), and the layers were separated. The upper organic layer (containing product) was transferred to a separate vessel while the reactor was rinsed with water and isopropanol. The organic layer was then transferred through an inline 5 μm Teflon® cartridge back into the clean 60 L reactor. The filter line was washed with 4.0 L (2.0 volumes) of isopropanol into the 60 L reactor. An additional 12.0 L (6.0 volumes) of isoproponal was added to the 60 L reactor and heated to 40° C. Under reduced pressure (50 torr) the batch was concentrated down to approximately 6 L (3.0 volumes). The solution was cooled from 27° C. to 20° C. in a linear manner over 10 minutes. Water (4.0 L, 2.0 volumes) was added at 20° C. over 30 minutes followed by Piperazine Nitro Freebase seed (18 g, 0.06 mol, 0.01 equiv). The mixture was aged for 5 minutes and the remaining water (24.0 L, 12.0 volumes) was added over 90 minutes. After holding overnight at 20° C., the supernatant concentration of Piperazine Nitro Freebase was measured (<10 mg/mL). The mixture was filtered through an aurora filter equipped with a 12 μm Teflon® cloth. The filter cake was washed with a mixture of water (3.3 L, 1.65 volumes) and isopropanol (700 mL, 0.35 volumes) and dried to constant weight (defined as ≤1.0% weight loss for 2 consecutive TGA measurements over a period of 2 hours) on filter with vacuum and a nitrogen sweep (48 h). The combined losses of Piperazine Nitro Freebase in the mother liquors and the wash were approximately 7.5%. Piperazine Nitro Freebase was isolated 1.67 kg in 92.5% corrected yield with 100.0 wt % and 99.4% LCAP purity.

Synthesis of the API SM Phenyl Carbamate-HCl

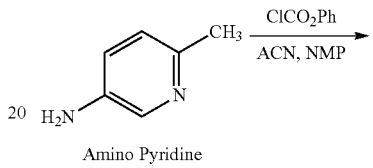

Amino Pyridine

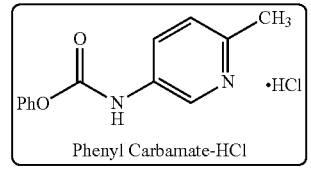

Phenyl Carbamate-HCl

A 60 L, glass-lined, jacketed reactor set at 20° C. under nitrogen atmosphere and vented through a scrubber (containing 5N NaOH) was charged with 2.5 kg of Amino Pyridine (1.0 equiv, 23.1 moles), followed by 25 L (19.6 kg, 10 vol) acetonitrile. After initiating agitation and (the endothermic) dissolution of the Amino Pyridine, the vessel was charged with 12.5 L of N-methyl-2-pyrrolidinone (12.8 kg, 5 vol). An addition funnel was charged with 1.8 L (0.6 equiv, 13.9 moles) phenyl chloroformate which was then added over 68 minutes to the solution of the Amino Pyridine keeping the internal temperature ≤30° C. The reaction was agitated for >30 minutes at an internal temperature of 20±5° C. The vessel was then charged with 61±1 g of seed as a slurry in 200 mL acetonitrile and aged for ≥30 min. The addition funnel was charged with 1.25 L (0.45 equiv, 9.7 moles) of phenyl chloroformate which was then added over 53 minutes to the reaction suspension while again keeping the temperature ≤30° C. The contents of the reactor were aged ≥30 hours at 20±5° C. After assaying the supernatant (≤15 mg/g for both product and starting material), the solids were filtered using an Aurora filter equipped with a 12 μm Teflon cloth. The mother liquor was forwarded to a $2^{nd}$ 60 L, glass-lined, jacketed reactor. The reactor and cake were rinsed with 1×10 L of 5:10 NMP/ACN and 1×10 L ACN. The washes were forwarded to the $2^{nd}$ reactor as well. The cake was dried under vacuum with a nitrogen bleed for ≥24 hours to afford 5.65 kg (90.2% yield) of the product, Phenyl Carbamate-HCl as an off-white solid in 98.8 wt % with 99.2% LCAP purity.

Phenyl(6-methylpyridin-3-yl)carbamate hydrochloride (Phenyl Carbamate-HCl) $^1$H NMR (400 MHz, DMSO-$d_6$) δ ppm 11.24 (s, 1H), 8.81 (s, 1H), 8.41 (d, 1H, J=8.8 Hz), 7.85 (d, 1H, J=8.8 Hz), 7.48-7.44 (m, 2H), 7.32-7.26 (m, 3H), 2.69 (s, 3H); $^{13}$C NMR (100 MHz, DMSO-$d_6$) δ ppm 151.66, 150.01, 147.51, 136.14, 133.79, 129.99, 129.49, 127.75, 125.87, 121.70, 18.55: HR-MS: Calculated for $C_{13}H_{12}N_2O_2$: 228.0899. $M+H^+$=229.0972; Observed mass: 229.0961

GMP Steps

Methyl 4-(3-amino-2-fluorobenzyl)piperazine-1-carboxylate (Piperazine Aniline)

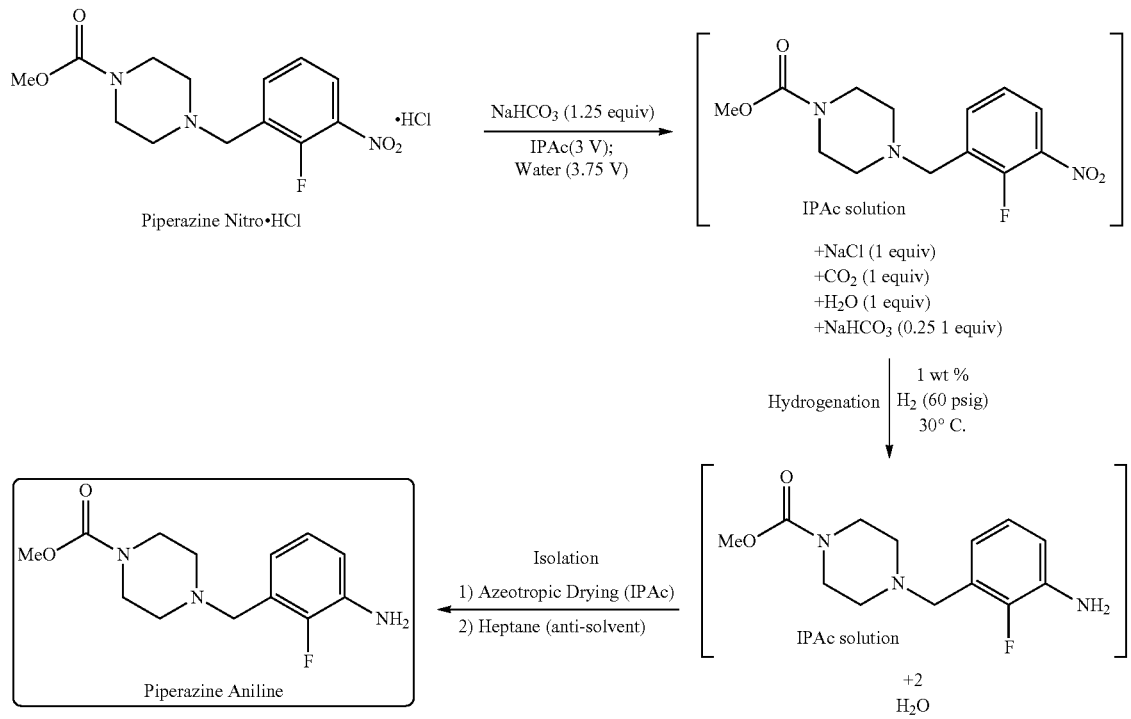

To a 100-L jacketed glass-lined reactor were added methyl 4-(2-fluoro-3-nitrobenzyl)piperazine-1-carboxylate hydrochloride (2.00 kg, 1.00 equiv) and isopropyl acetate (6.00 L, 3.00 Vol with-respect to starting material). The resulting slurry was agitated under a nitrogen sweep. To the mixture was added dropwise over 45±30 min: 7.7% w/w aqueous sodium bicarbonate solution (629 g, 1.25 equiv of sodium bicarbonate dissolved in 7.50 L water), maintaining an internal temperature of 20±5° C. by jacket control (NOTE: addition is endothermic, and may evolve up to 1 equiv of carbon dioxide gas). The mixture was stirred for ≥15 min, resulting in a clear biphasic mixture. Agitation was stopped and the layers were allowed to settle.

The bottom (aqueous) layer was drained and analyzed by pH paper to ensure that the layer is pH>6. Quantitative HPLC analysis of the upper (organic) layer revealed 97-100% assay yield of the methyl 4-(2-fluoro-3-nitrobenzyl)piperazine-1-carboxylate freebase (1.73-1.78 kg). The upper (organic) layer was transferred through an in-line filter into a 20-L Hastelloy® hydrogenator, and the 100-L reactor and lines were rinsed with an additional aliquot of isopropyl acetate (2.00 L, 1.00 Vol). The hydrogenator was purged with nitrogen and vented to atmospheric pressure. To the reaction mixture was added a slurry of 5.0 wt % palladium on carbon (20.0 g, Strem/BASF Escat™ 1421, approx 50% water) in isopropyl acetate (400 mL), followed by a 400 mL rinse. The resulting reaction mixture was diluted with an additional aliquot of isopropyl acetate (1.2 L; total isopropyl acetate amount is 10.0 L, 5.00 Vol). The hydrogenator was purged three times with nitrogen (pressurized to 60±10 psig, then vented to atmospheric pressure), then pressurized to 60±5 psig with hydrogen. The reaction mixture was stirred at <100 rpm at 30±5° C. while maintaining 60±5 psig hydrogen, for >2 hours until reaction was deemed complete.

This temperature and pressure correspond to a measured kLa value of approx 0.40 in a 20-L Hydrogenator. End of reaction is determined by dramatic decrease in hydrogen consumption accompanied by a relief in the heat evolution of the reaction. To control potential dimeric impurities, the reaction is continued for at least 30 minutes after this change in reaction profile, and HPLC analysis is performed to confirm that >99.5% conversion of the hydroxyl-amine to the aniline is achieved.

At the end of reaction, the hydrogenator was purged with nitrogen twice (pressurized to 60±10 psig, then vented to atmospheric pressure). The crude reaction mixture was filtered through a 5 μm filter followed by a 0.45 μm filter in series, into a 40-L glass-lined reactor. The hydrogenator and lines were washed with an additional aliquot of isopropyl acetate (2.00 L). Quantitative HPLC analysis of the crude reaction mixture revealed 95-100% assay yield (1.52-1.60 kg aniline product). The reaction mixture was distilled under reduced pressure (typically 250-300 mbar) at a batch temperature of 50±5° C. until the total reaction volume was approximately 8.00 L (4.00 Vol). The batch was subjected to a constant-volume distillation at 50±5° C., 250-300 mbar, by adding heptane to control the total batch volume. After approximately 8.00 L (4.00 Vol) of heptane were added, GC analysis indicated that the solvent composition was approximately 50% isopropyl acetate, 50% heptane. Vacuum was broken, and the internal batch temperature was maintained at 50±5° C. To the reaction mixture was added a slurry of seed (20.0 grams of product methyl 4-(3-amino-2-fluorobenzyl)piperazine-1-carboxylate, in a solvent mixture of 80 mL heptane and 20 mL isopropyl acetate). The resulting slurry was allowed to stir at 50±5° C. for 2±1 hours, then cooled to 20±5° C. over 2.5±1.0 h. Additional heptane (24.0 L, 12.0 Vol) was added dropwise over 2 hours, and the batch was allowed to stir at 20±5° C. for ≥1 hours (typically overnight). Quantitative HPLC analysis of this filtered supernatant revealed <5 mg/mL product in solution, and the product crystals were 50-400 μm birefringent rods. The reaction slurry was filtered at 20° C. onto a filter cloth, and the cake was displacement-washed with heptane (6.00 L, 2.00 Vol). The cake was dried on the filter under nitrogen sweep at ambient temperature for >4 hours, until sample dryness was confirmed by LOD analysis (indicated <1.0 wt % loss). The product methyl 4-(3-amino-2-fluorobenzyl)piperazine-1-carboxylate (1.56 kg) was isolated as a pale-yellow powder in 86% yield at 99.8 wt % by HPLC with 100.0 $LCAP_{210}$. [Analysis of the combined filtrates and washes revealed 108 grams (7.0%) of product lost to the mother liquors. The remaining mass balance is comprised of product hold-up in the reactor (fouling).] $^1$H NMR (DMSO-$d_6$, 400 MHz) δ: 6.81 (dd, J=7.53, 7.82 Hz, 1H), 6.67 (m, 1H), 6.49 (m, 1H), 5.04 (s, 2H), 3.58 (s, 3H), 3.45 (m, 2H), 3.34 (m, 4H), 2.33 (m, 4H). $^{19}$F NMR ($d_6$-DMSO, 376 MHz) δ: −140.2. $^{13}$C NMR ($d_6$-DMSO, 125 MHz) δ: 155.0, 150.5, 148.2, 136.2 (m), 123.7 (m), 117.6, 115.1, 73.7, 54.9 (m), 52.1 (m), 43.4. mp=89.2° C.

Omecamtiv Mecarbil Dihydrochloride Hydrate Procedure

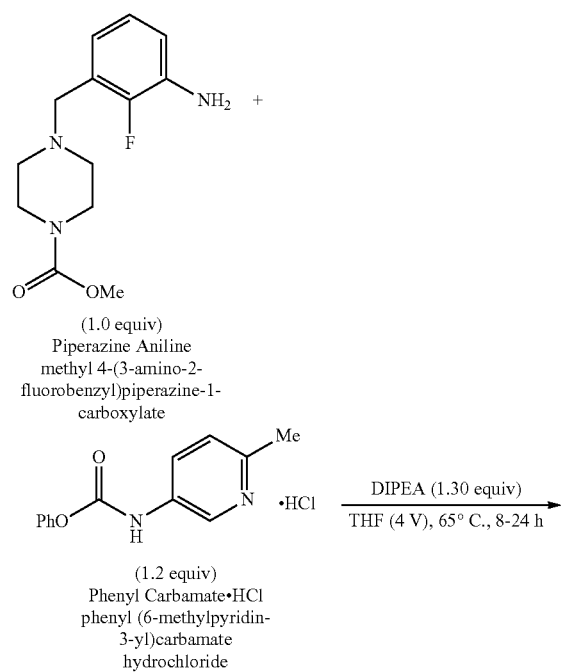

(1.0 equiv)
Piperazine Aniline
methyl 4-(3-amino-2-fluorobenzyl)piperazine-1-carboxylate (1.2 equiv)
Phenyl Carbamate•HCl
phenyl (6-methylpyridin-3-yl)carbamate hydrochloride DIPEA (1.30 equiv)
THF (4 V), 65° C., 8-24 h

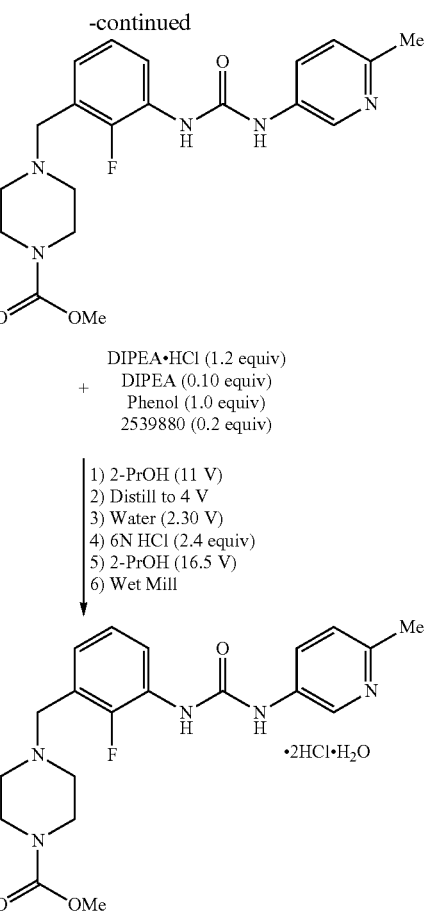

DIPEA•HCl (1.2 equiv)
DIPEA (0.10 equiv)
Phenol (1.0 equiv)
2539880 (0.2 equiv)

1) 2-PrOH (11 V)
2) Distill to 4 V
3) Water (2.30 V)
4) 6N HCl (2.4 equiv)
5) 2-PrOH (16.5 V)
6) Wet Mill

•2HCl•$H_2O$

To a 15 L glass lined reactor were charged methyl 4-(3-amino-2-fluoro-benzyl)piperazine-1-carboxylate (1,202 g, 4.50 mol), phenyl(6-methylpyridin-3-yl)carbamate hydrochloride (1,444 g, 5.40 mol), and tetrahydrofuran (4.81 L). The resulting slurry was agitated under a nitrogen sweep and N,N-diisopropylethylamine (1,019 L, 5.85 mol) was then charged to the slurry which resulted in a brown solution. The temperature of the solution was increased to 65° C. and agitated for 22 h, until <1% AUC piperazine aniline remained by HPLC analysis.

The batch was cooled to 50° C. and distilled under reduced pressure while maintaining the internal temperature of the vessel below 50° C. by adjusting vacuum pressure. 2-Propanol was added with residual vacuum at a rate to maintain a constant volume in the 15 L reactor. A total of 10.5 kg of 2-propanol was required to achieve <5% THF by GC. Water (2.77 kg) was then charged to the reactor followed by the addition of 6N HCl (1.98 kg) at a rate to maintain the internal temperature below 60° C. The reactor was brought to ambient pressure under a nitrogen sweep. The solution was then heated to 60° C., and transferred to a 60 L glass lined reactor through an inline filter. The 15 L reactor was then rinsed with 1:1 water/2-propanol (1.2 L) which was sent through the inline filter to the 60 L reactor.

The 60 L reactor was adjusted to 45° C. and a slurry of seed (114 g, 0.23 mol) in 2-propanol (0.35 L) was added to the reactor resulting in a slurry. The batch was aged at 45° C. for 1 h, followed by the addition of 2-propanol (3.97 kg) through an inline filter over 2 h. The batch was heated to 55° C. over 1 h and held for 0.25 h, then cooled back to 45° C. over 1 h and held overnight at 45° C. 2-propanol (11.71 kg)

was then added through an inline filter to the batch over 3 h. The batch was aged for 1 h and then cooled to 20° C. over 2 h and held at 20° C. for 0.5 h. The batch was then recirculated though a wet mill affixed with 1-medium and 2-fine rotor-stators operating at 56 Hz for 2.15 h, until no further particle size reduction was observed by microscopy.

The batch was then filtered through a 20" Hastelloy® filter fitted with a 12 um filter cloth under 500 torr vacuum. A wash solution of 95:5 2-propanol:water (1.82 L) was charged through an inline filter to the 60 L reactor, then onto the filter. A second wash of 2-propanol (2.85 L) was charged through an inline filter to the 60 L reactor, then onto the filter. The batch was then dried under 5 psi humidified nitrogen pressure until <5,000 ppm 2-propanol, and 2.5-5% water remained. The final solid was discharged from the filter to afford 2.09 kg of methyl 4-(2-fluoro-3-(3-(6-methylpyridin-3-yl)ureido)benzyl)piperazine-1-carboxylate as an off-white crystalline solid in 89% yield at 99.88 wt % by HPLC, 100.0% AUC. Total losses to liquors was 0.10 kg (4.7%).

DSC: $T_{onset}$=61.7° C., $T_{max}$=95.0° C.; TGA=2.2%, degradation onset=222° C.; $^1$H HMR ($D_2O$, 500 MHz) δ 8.87 (s, 1H), 8.18 (d, J=8.9 Hz, 1H), 7.83 (t, J=7.5 Hz, 1H), 7.71 (d, J=8.8 Hz, 1H), 7.35-7.29 (m, 2H), 4.48 (s, 2H), 4.24 (br s, 2H), 3.73 (s, 3H), 3.31 (br s, 6H), 2.68 (s, 3H); $^{13}$C HMR ($D_2O$, 150 MHz) δ 156.8, 154.2, 153.9 (J=249 Hz), 147.8, 136.3, 136.1, 130.1, 129.4, 128.0, 127.2, 125.5 (J=11.8 Hz), 125.1 (J=4.2 Hz), 116.1 (J=13.5 Hz), 53.54, 53.52, 53.49, 50.9, 40.5, 18.2.

Example 1: Immediate Release Formulation

TABLE 1

| Material | Theo. w/w % | Theo. mg/unit |
|---|---|---|
| Intra-granulation | | |
| omecamtiv mecarbil dihydrochloride hydrate | 12.28 | 30.70 |
| Fumaric acid | 12.28 | 30.70 |
| Microcrystalline cellulose, Avicel ® PH 101 | 38.00 | 95.00 |
| Lactose monohydrate, Impalpable 313 | 29.94 | 74.85 |
| Hydroxypropyl cellulose, Klucel EXF | 2.00 | 5.00 |
| Croscarmellose sodium, Ac-Di-Sol | 2.50 | 6.25 |
| Extra-granulation | | |
| Croscarmellose sodium, Ac-Di-Sol | 2.50 | 6.25 |
| Magnesium stearate | 0.50 | 1.25 |
| Total | 100.00% | 250.00 |

Example 2: Composition of Omecamtive Mecarbil Dihydrochloride Hydrate 25-mg MR Swellable Core Tablet Brief Description of SCT Tablet Manufacturing Process Omecamtiv mecarbil dihydrochloride hydrate 25-mg MR swellable core tablets are manufactured using a dry granulation process for the drug layer blend and a direct compression process for the sweller layer blend. The dry granulation process was found to achieve uniform distribution of the drug substance in the formulation, improve the flow properties of the blend, and maintain acceptable compressibility for tablet manufacture in a rotary bilayer tablet press. Tablet coating is performed in a pan coater capable of solvent processing. A $CO_2$ laser system creates the hole in the CA/PEG tablet coating.

Manufacturing of omecamtiv mecarbil dihydrochloride hydrate 25-mg MR swellable core tablets begins with manufacturing of the bilayer core tablet. Sweller layer blend and drug layer blend are prepared and compressed to form the bi-layer tablet. An insoluble, semi-permeable coating is then applied to the tablets. A laser-drilled hole is then made on the drug layer side of the tablet to facilitate osmotic-based release of the drug.

Step Descriptions

Step 1. A tumble blender is used to make the sweller layer blend from polyethylene oxide WSR coagulant, sodium chloride, microcrystalline cellulose, and FD&C #2 Blue Lake.

Step 2. The sweller layer blend from Step 1 is de-agglomerated with a conical mill equipped with a 0.045-inch round-hole screen.

Step 3. The sweller layer blend from Step 2 is returned to the tumble blender and blended with magnesium stearate. The sweller layer blend is held until ready for bi-layer tablet compression.

Step 4. A tumble blender is used to prepare the drug layer blend beginning from omecamtiv mecarbil dihydrochloride hydrate and polyethylene oxide WSR N-80.

Step 5. The blend from Step 4 is de-agglomerated using a conical mill equipped with a 0.045-inch round-hole screen.

Step 6. The blend from Step 5 is returned to the tumble blender and blended.

Step 7. Magnesium stearate is charged to the tumble blender and blended.

Step 8. The drug layer blend from Step 7 is roller compacted using a roller compactor. Throughput is monitored during the process.

Step 9. The resultant compacts from Step 8 are dry sized into granules using a conical mill equipped with a 0.040-inch grating screen.

Step 10. The granules from Step 9 are placed in a tumble blender and blended with magnesium stearate. The drug layer blend is held until ready for bi-layer tablet compression.

Step 11. A rotary press is configured for bi-layer tablet compression and the sweller layer blend and drug layer blend are compressed into a single bi-layer tablet. Drug layer weight, total tablet weight, thickness, hardness, and appearance are monitored periodically throughout the compression. Finally, bi-layer tablets are de-dusted and passed through a metal checker.

Step 12. A water-insoluble, semi-permeable membrane coating is prepared in a solution tank by dissolving cellulose acetate and polyethylene glycol in acetone and purified water.

Step 13. The semi-permeable membrane coating is applied to the bi-layer tablets using a pan coater to a target percent weight gain.

Step 14. The coated bi-layer tablets from Step 13 are placed into an oven for secondary drying to remove residual solvents. An in-process test is used to confirm acceptable residual solvent levels.

Step 15. A single orifice is drilled through the semi-permeable coating on the drug layer side of the tablets using a laser drill. Tablets are inspected.

Step 16. Tablets are packaged.

TABLE 2

Omecamtiv mecarbil dihydrochloride hydrate 25 mg slow release MR SCT tablets F1

| Component and Grade | Percentage (% w/w) 25-mg | Quantity (mg/tablet) 25-mg | Function | Reference to Standard |
|---|---|---|---|---|
| Tablet Core - Drug Layer | | | | |
| Omecamtiv mecarbil dihydrochloride hydrate (free base)[a] | 15.33 (12.50) | 30.664 (25.000) | Active | In-house |
| Polyethylene Oxide N-80, PolyOx WSR N-80 | 51.00 | 102.0 | Drug layer polymer | Ph. Eur., USP/NF, JP |
| Magnesium stearate | 0.335 | 0.670 | Lubricant | Ph. Eur., USP/NF, JP |
| Total drug layer | 66.67 | 133.33 | — | — |
| Tablet Core - Sweller Layer | | | | |
| Polyethylene Oxide Coagulant, PolyOx WSR Coagulant | 21.60 | 43.20 | Sweller layer polymer | Ph. Eur., USP/NF, JP |
| Sodium chloride | 6.67 | 13.33 | Osmotic agent | Ph. Eur., USP/NF, JP |
| Microcrystalline cellulose, Avicel PH 200 | 4.80 | 9.60 | Diluent | Ph. Eur., USP/NF, JP |
| Magnesium stearate | 0.165 | 0.330 | Lubricant | Ph. Eur., USP/NF, JP |
| FD&C #2 Blue Lake | 0.100 | 0.200 | Colorant | Manuf. CofA |
| Total sweller layer | 33.33 | 66.66 | — | — |
| Total unit dose | 100.00 | 200.0 | — | — |
| Semi-Permeable Membrane Coating | | | | |
| Cellulose acetate, CA-398-10 | 9.45 | 18.90 | Functional coating | Ph. Eur., USP/NF |
| Polyethylene Glycol 3350, Carbowax ® 3350 | 1.05 | 2.100 | Pore former | Ph. Eur., USP/NF |
| Acetone | —[b] | —[b] | Coating solvent | USP/NF |
| Purified water | —[b] | —[b] | Coating solvent | USP |
| Total unit dose | 110.50 | 221.0 | — | — |

[a]The molecular weight of omecamtiv mecarbil dihydrochloride hydrate and omecamtiv mecarbil free base are 492.37 g/mol and 401.43 g/mol, respectively. Actual quantity used may be adjusted by the assay of the drug substance lot.
[b]Removed from process via drying after each respective intermediate step.

Example 3

TABLE 3

Invented omecamtiv mecarbil dihydrochloride hydrate 25 mg fast release MR SCT tablets F2

| Component and Grade | Percentage (% w/w) 25-mg | Quantity (mg/tablet) 25-mg | Function | Reference to Standard |
|---|---|---|---|---|
| Tablet Core - Drug Layer | | | | |
| omecamtiv mecarbil dihydrochloride hydrate (free base)[a] | 15.33 (12.50) | 30.664 (25.000) | Active | In-house |
| Polyethylene Oxide N-80, PolyOx WSR N-80 | 51.00 | 102.0 | Drug layer polymer | Ph. Eur., USP/NF, JP |
| Magnesium stearate | 0.335 | 0.670 | Lubricant | Ph. Eur., USP/NF, JP |
| Total drug layer | 66.67 | 133.33 | — | — |
| Tablet Core - Sweller Layer | | | | |
| Polyethylene Oxide Coagulant, PolyOx WSR Coagulant | 21.60 | 43.20 | Sweller layer polymer | Ph. Eur., USP/NF, JP |
| Sodium chloride | 6.67 | 13.33 | Osmotic agent | Ph. Eur., USP/NF, JP |
| Microcrystalline cellulose, Avicel PH 200 | 4.80 | 9.60 | Diluent | Ph. Eur., USP/NF, JP |
| Magnesium stearate | 0.165 | 0.330 | Lubricant | Ph. Eur., USP/NF, JP |
| FD&C #2 Blue Lake | 0.100 | 0.200 | Colorant | Manuf. CofA |
| Total sweller layer | 33.33 | 66.66 | — | — |
| Total unit dose | 100.00 | 200.0 | — | — |
| Semi-Permeable Membrane Coating | | | | |
| Cellulose Acetate, CA-398-10 | 8.40 | 16.80 | Functional coating | Ph. Eur., USP/NF |
| Polyethylene Glycol 3350, Carbowax ® 3350 | 2.10 | 4.200 | Pore former | Ph. Eur., USP/NF |
| Acetone | —[b] | —[b] | Coating solvent | USP/NF |
| Purified water | —[b] | —[b] | Coating solvent | USP |
| Total unit dose | 110.50 | 221.0 | — | — |

[a]The molecular weight of omecamtiv mecarbil dihydrochloride hydrate and omecamtiv mecarbil free base are 492.37 g/mol and 401.43 g/mol, respectively. Actual quantity used may be adjusted by the assay of the drug substance lot.
[b]Removed from process via drying after each respective intermediate step.

The foregoing is merely illustrative of the invention and is not intended to limit the invention to the disclosed formulations. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed:
1. A pharmaceutical tablet formulation comprising:
   a drug layer, comprising omecamtiv mecarbil dihydrochloride hydrate;
   a sweller layer; and
   a semi-permeable membrane coating having at least one delivery port,
wherein the semi-permeable membrane coating comprises 80% insoluble polymer and 20% pore forming polymer.
2. A pharmaceutical tablet formulation according to claim 1, wherein the drug layer comprises:

omecamtiv mecarbil dihydrochloride hydrate;
a drug layer polymer; and
a lubricant.

3. A pharmaceutical tablet formulation according to claim 1, wherein the sweller layer comprises:
a sweller layer polymer;
an osmotic agent;
a diluent; and
a lubricant.

4. A pharmaceutical tablet formulation according to claim 1, where the
insoluble polymer comprises cellulose acetate.

5. A pharmaceutical tablet formulation according to claim 1, wherein the pore forming polymer comprises polyethylene glycol.

6. A pharmaceutical tablet formulation comprising:
a drug layer comprising:
omecamtiv mecarbil dihydrochloride hydrate;
a drug layer polymer; and
a lubricant;
a sweller layer comprising:
a sweller layer polymer;
an osmotic agent;
a diluent; and
a lubricant; and
a semi-permeable membrane coating having at least one delivery port comprising:
an insoluble polymer comprising cellulose acetate; and
a pore forming polymer comprising polyethylene glycol,
wherein the semi-permeable membrane coating comprises 80% the insoluble polymer and 20% the pore forming polymer.

7. A pharmaceutical tablet formulation comprising
a drug layer comprising:
14-17 (w/w%) omecamtiv mecarbil dihydrochloride hydrate;
48-55 (w/w%) polyethylene oxide; and
0.1-0.5% (w/w%) lubricant;
a sweller layer comprising:
18-25 (w/w%) polyethylene oxide;
4-9 (w/w%) an osmotic agent;
3-6 (w/w%) microcrystalline cellulose; and
0.1-0.5 (w/w%) lubricant; and
a semi-permeable membrane having at least one delivery port comprising:
8-10 (w/w%) cellulose acetate;
0.5-3 (w/w%) polyethylene glycol.

8. The pharmaceutical tablet formulation of claim 7, wherein the polyethylene glycol of the semi-permeable membrane has an average molecular weight of 3350.

9. The pharmaceutical tablet formulation of claim 7, wherein the osmotic agent comprises sodium chloride.

10. The pharmaceutical tablet formulation of claim 7, having one to 10 delivery ports.

11. The pharmaceutical tablet formulation according to claim 1, wherein the tablet comprises 14-17 (w/w%) omecamtiv mecarbil dihydrochloride hydrate.

12. The pharmaceutical tablet formulation according to claim 1, wherein the insoluble polymer comprises cellulose acetate and the pore forming polymer comprises polyethylene glycol.

13. The pharmaceutical tablet formulation according to claim 1, having one to 10 delivery ports.

14. The pharmaceutical tablet formulation according to claim 12, wherein the tablet comprises 14-17 (w/w%) omecamtiv mecarbil dihydrochloride hydrate.

15. The pharmaceutical tablet formulation according to claim 14, wherein the polyethylene glycol of the semi-permeable membrane has an average molecular weight of 3350.

* * * * *